United States Patent
Chai et al.

(10) Patent No.: US 10,648,095 B2
(45) Date of Patent: May 12, 2020

(54) PRODUCTION METHOD OF MOLD, MANUFACTURING METHOD OF PATTERN SHEET, PRODUCTION METHOD OF ELECTROFORM, PRODUCTION METHOD OF MOLD USING ELECTROFORM, AND ORIGINAL

(71) Applicant: FUJIFILM Corporation, Tokyo (JP)

(72) Inventors: Satoshi Chai, Kanagawa (JP); Kenji Ichikawa, Kanagawa (JP); Ryo Hibino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 280 days.

(21) Appl. No.: 15/592,199

(22) Filed: May 11, 2017

(65) Prior Publication Data
US 2017/0327963 A1    Nov. 16, 2017

(30) Foreign Application Priority Data
May 13, 2016  (JP) .................. 2016-097270

(51) Int. Cl.
*B29C 33/42* (2006.01)
*C25D 1/10* (2006.01)
(Continued)

(52) U.S. Cl.
CPC ............ *C25D 1/10* (2013.01); *B29C 33/3857* (2013.01); *B29C 33/3892* (2013.01);
(Continued)

(58) Field of Classification Search
None
See application file for complete search history.

(56) References Cited

U.S. PATENT DOCUMENTS 8,671,544 B2 * 3/2014 Xu .................... A61M 37/0015
264/154
9,789,656 B2   10/2017 Furuta et al.
(Continued)

FOREIGN PATENT DOCUMENTS

JP    2007-535343    12/2007
JP    2010213845     9/2010
(Continued)

OTHER PUBLICATIONS

English translation JP2010-213845 (Year: 2010).*
English translation JP2011-083993 (Year: 2011).*
"Search Report of European Counterpart Application," dated Sep. 8, 2017, p. 1-p. 5.
Office Action of Japan Counterpart Application, with English translation thereof, dated Apr. 11, 2019, pp. 1-11.
(Continued)

*Primary Examiner* — Stefanie S Wittenberg
(74) *Attorney, Agent, or Firm* — JCIPRNET

(57) ABSTRACT

Provided are a production method of a mold, a manufacturing method of a pattern sheet, a production method of an electroform, a production method of a mold using an electroform, and an original. The production method includes: preparing an original having an inclined portion which is formed in an enclosed shape on an outer peripheral portion of a protruding pattern formed at a center portion on a base and gradually increases in thickness from inside toward outside, and a thermoplastic resin sheet; and forming a recessed pattern on the thermoplastic resin sheet by pressing the original which is heated against the thermoplastic resin sheet at a position where a flat surface of the original and a surface of the thermoplastic resin sheet are separated from each other, cooling the original in the state where the original is pressed, and separating the original from the thermoplastic resin sheet.

11 Claims, 25 Drawing Sheets

(51) Int. Cl.
  *B29C 33/38* (2006.01)
  *B29C 33/40* (2006.01)
  *B29C 39/02* (2006.01)
  *B29C 39/26* (2006.01)
  *B29C 39/36* (2006.01)
  *C25D 1/20* (2006.01)
  *B29L 31/00* (2006.01)
  *A61M 37/00* (2006.01)
  *B29K 105/00* (2006.01)
  *B29L 7/00* (2006.01)

(52) U.S. Cl.
  CPC ............ *B29C 33/40* (2013.01); *B29C 33/424* (2013.01); *B29C 39/026* (2013.01); *B29C 39/26* (2013.01); *B29C 39/36* (2013.01); *C25D 1/20* (2013.01); *A61M 2037/0053* (2013.01); *B29K 2105/0035* (2013.01); *B29L 2007/00* (2013.01); *B29L 2031/756* (2013.01); *B29L 2031/7544* (2013.01)

(56) References Cited

U.S. PATENT DOCUMENTS

| | | |
|---|---|---|
| 2010/0305516 A1 | 12/2010 | Xu et al. |
| 2013/0328224 A1* | 12/2013 | Furuta ................. B29C 33/3857 264/2.5 |
| 2016/0082626 A1 | 3/2016 | Kato et al. |

FOREIGN PATENT DOCUMENTS

| | | |
|---|---|---|
| JP | 2011-083993 | 4/2011 |
| JP | 2012055343 | 3/2012 |
| WO | 2012121221 | 9/2012 |
| WO | 2014196522 | 12/2014 |

OTHER PUBLICATIONS

"Office Action of Japan Counterpart Application," dated Jun. 10, 2019, with English translation thereof, p. 1-p. 4.

* cited by examiner

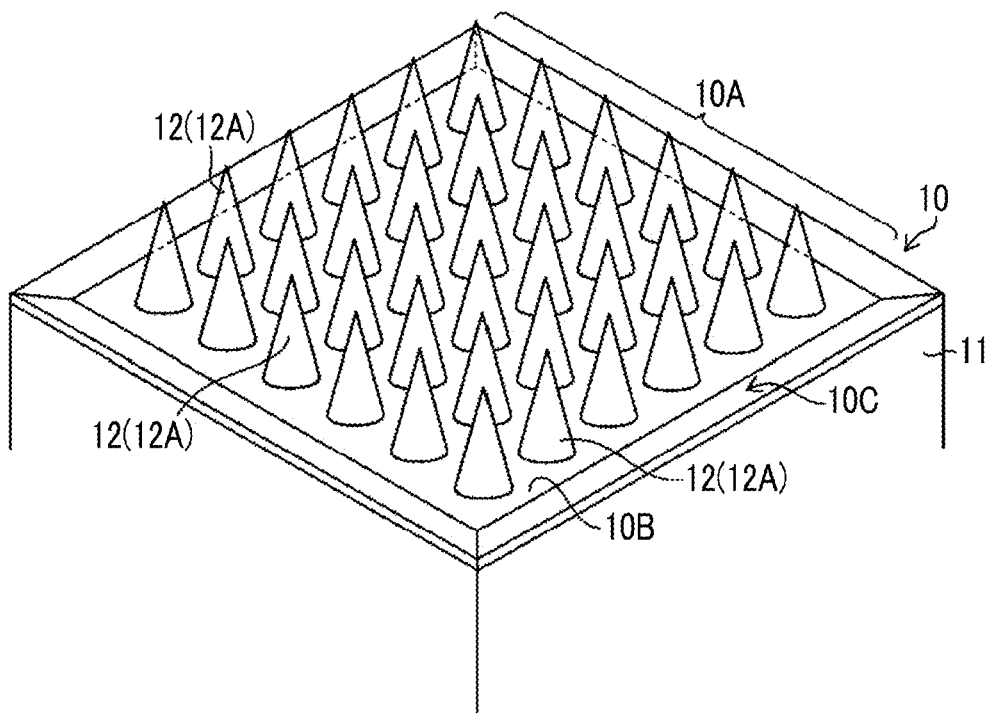

PRODUCTION METHOD OF MOLD, MANUFACTURING METHOD OF PATTERN SHEET, PRODUCTION METHOD OF ELECTROFORM, PRODUCTION METHOD OF MOLD USING ELECTROFORM, AND ORIGINAL

CROSS-REFERENCE TO RELATED APPLICATIONS

The present application claims priority under 35 U.S.C. § 119 to Japanese Patent Application No. 2016-097270, filed on May 13, 2016. The above application is hereby expressly incorporated by reference, in its entirety, into the present application.

BACKGROUND OF THE INVENTION

1. Field of the Invention

The present invention relates to a production method of a mold, a manufacturing method of a pattern sheet, a production method of an electroform, a production method of a mold using an electroform, and an original.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as fine needles or small needles) which contain drugs and are biodegradable. By attaching this microneedle array to the skin, each microneedle pierces the skin, these microneedles are absorbed in the skin such that the drugs contained in each microneedle can be administered into the skin. Microneedle arrays are also called percutaneous absorption sheets.

In order to produce a formed product having a fine protruding pattern like the microneedle array as described above, a resin mold having the inverted shape is formed from an original having a fine protruding pattern, and a formed product is produced from the mold. There is a demand for improving the productivity of formed products having fine patterns, and various proposals have been made.

JP2007-535343A discloses a production method of a mold base for manufacturing microneedles. In the technique described in JP2007-535343A, a mold base for manufacturing microneedles is produced by pressing a master model having master model needle arrays against a mold plate for manufacturing microneedles, and a formed product having a fine pattern is produced by using the mold base for manufacturing microneedles.

JP2011-083993A discloses transferring a transfer pattern formed on a mold to a plurality of points of a thermoplastic resin. In the technique described in JP2011-083993A, a heated mold is pressed against a thermoplastic resin and is cooled, and the mold is separated from the thermoplastic resin, thereby transferring the transfer pattern of the mold to the thermoplastic resin. Furthermore, moving the heated mold, pressing the mold against the thermoplastic resin and cooling the mold, and separating the mold from the thermoplastic resin are repeated, thereby transferring the transfer pattern of the mold to the thermoplastic resin.

SUMMARY OF THE INVENTION

In the technique described in JP2007-535343A, the master model (original) having a plurality of the master model needle arrays (for example, 8×8) is used. That is, a large master model is required, and thus there is concern that the number of operations for producing the master model may increase.

In the technique described in JP2011-083993A, the transfer pattern of the mold is transferred to the thermoplastic resin while pressing the flat surface of the mold against the thermoplastic resin. Therefore, there may be cases where the thermoplastic resin is raised at the end portion of the mold, and as a result, there is concern that a stepped portion may be formed between the molds. When a duplicate mold (also called an electroform) is formed by electroforming or a formed product such as a percutaneous absorption sheet is manufactured, there may be cases where the stepped portion adversely affects the precision and productivity of the duplicate mold or the formed product.

The present invention has been made taking the above circumstances into consideration, and an object thereof is to provide a production method of a mold, a manufacturing method of a pattern sheet, a production method of an electroform, a production method of a mold using an electroform, and an original capable of preventing peeling failure during production of a duplicate product or formed product from a mold and improving the releasability of the original itself by preventing the generation of a stepped portion at an end portion of a recessed pattern of the surface of the mold.

According to an aspect of the present invention, there is provided a production method of a mold comprising: a preparation process of preparing an original having an inclined portion which is formed in an enclosed shape on an outer peripheral portion of a protruding pattern formed at a center portion on a base and gradually increases in thickness from the inside toward the outside, and a thermoplastic resin sheet; and a forming process of forming a recessed pattern having an inverted shape of the protruding pattern on the thermoplastic resin sheet by pressing the original which is heated against the thermoplastic resin sheet at a position where the inclined portion of the original and a surface of the thermoplastic resin sheet are in close contact with each other, cooling the original in the state in which the original is pressed, and separating the original from the thermoplastic resin sheet.

Accordingly, the generation of a stepped portion at the end portion of the recessed pattern of the surface of the produced mold can be prevented.

In a preferred aspect of the present invention, it is preferable that an alignment process of determining a position at which the original is to be pressed against the thermoplastic resin sheet by moving the original and the thermoplastic resin sheet relative to each other, and the forming process are repeatedly performed. Accordingly, the generation of a stepped portion between the recessed patterns can be prevented, and a large mold having a plurality of the recessed patterns with a single original can be produced.

In a preferred aspect of the present invention, it is preferable that the inclined portion has a vertical sectional shape formed in a right-angled triangle such that the thickness thereof linearly increases from the inside toward the outside. Accordingly, the generation of a stepped portion can be prevented.

In a preferred aspect of the present invention, it is preferable that the inclined portion has a vertical sectional shape formed in an arcuate shape such that the thickness thereof increases in an arc shape from the inside toward the outside and thereafter the increase in thickness gradually decreases. Accordingly, the generation of a stepped portion can be further prevented.

In a preferred aspect of the present invention, the original has a flat portion which is formed to be connected to an inclination terminal of the inclined portion.

It is preferable that, when the original is pressed against the thermoplastic resin sheet, a position of the surface of the thermoplastic resin sheet is detected, and the original is pushed from the position of the surface of the thermoplastic resin sheet by a certain amount.

It is preferable that, when the original is pressed against the thermoplastic resin sheet, a pressure applied to the original is measured and is compared to a certain pressure value which is set, and the amount of the original being pushed is determined.

According to another aspect of the present invention, there is provided a manufacturing method of a pattern sheet having a protruding pattern, comprising: a process of producing a mold using the above-described production method; a supplying process of supplying a polymer solution to a recessed pattern of the mold; a drying process of drying the polymer solution to form a polymer sheet; and a polymer sheet peeling process of peeling the polymer sheet from the mold.

According to another aspect of the present invention, there is provided a production method of an electroform having a protruding pattern, comprising: a process of producing a mold using the above-described production method; an electroforming process of forming a metal body on a recessed pattern of the mold by an electroforming method; and a peeling process of peeling the metal body from the mold.

According to another aspect of the present invention, there is provided a production method of a mold, comprising: a process of producing an electroform using the above-described production method; and a process of, by using the electroform having a protruding pattern, producing a mold which has a recessed pattern which is an inverted shape of the protruding pattern of the electroform and is made of a resin.

According to another aspect of the present invention, there is provided a manufacturing method of a pattern sheet having a protruding pattern, comprising: a process of producing a mold using the production method of an electroform described above; a supplying process of supplying a polymer solution to a recessed pattern of the mold; a drying process of drying the polymer solution to form a polymer sheet; and a peeling process of peeling the polymer sheet from the mold.

According to an aspect of the present invention, there is provided an original which is pressed against a surface of a thermoplastic resin sheet to transfer a protruding pattern onto the thermoplastic resin sheet, the original comprising: an inclined portion which is formed in an enclosed shape on an outer peripheral portion of the protruding pattern formed at a center portion on a base and gradually increases in thickness from the inside toward the outside.

Accordingly, when a mold is produced using the original, the generation of a stepped portion at the end portion of a recessed pattern of the surface of the mold can be prevented, and the peeling property of the original itself is also improved.

Furthermore, a preferred aspect of the original further comprises a flat portion which is formed to be connected to an inclination terminal of the inclined portion.

According to the production method of a mold, the manufacturing method of a pattern sheet, the production method of an electroform, the production method of a mold using an electroform, and the original of the present invention, the generation of a stepped portion at the end portion of the recessed pattern of the mold can be prevented.

Accordingly, peeling failure during production of a duplicate product or formed product from a mold can be prevented, and the releasability of the original itself can be improved.

BRIEF DESCRIPTION OF THE DRAWINGS

FIG. 1 is a perspective view illustrating an aspect of an original according to an embodiment of the present invention.

DESCRIPTION OF THE PREFERRED EMBODIMENTS

Figure 2A:
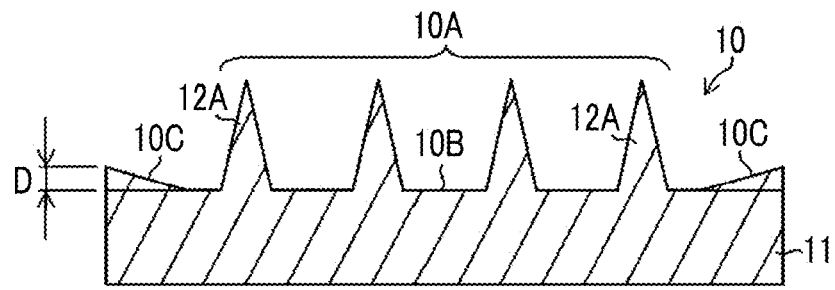
FIG. 2A is a vertical sectional view of an original having a linear inclined portion.

Hereinafter, preferred embodiments of the present invention will be described with reference to the accompanying drawings. The present invention is described by the following preferred embodiments.

Modifications can be made by various methods without departing from the scope of the present invention, and other embodiments than this embodiment can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

[Original] (First Embodiment of Original)

FIG. 1 is a perspective view illustrating a first embodiment of an original of the present invention.

As illustrated in FIG. 1, the first embodiment of the original 10 includes a protruding pattern 10A formed at the center portion on one flat surface 10B of a base 11, and an inclined portion 10C formed on the outer peripheral portion of the protruding pattern 10A.

The original 10 having the protruding pattern 10A and the inclined portion 10C is produced, for example, by machining a metal substrate, which is to become the original 10, using a cutting tool such as a diamond insert bite. As the metal substrate, stainless steel, an aluminum alloy, Ni, or the like may be used.

The protruding pattern 10A of the original 10 is basically the same as the protruding pattern of a pattern sheet (a formed product such as a percutaneous absorption sheet) to be produced. The protruding pattern 10A refers to a state in which a protrusion 12 protruding in a direction away from the flat surface 10B of the original 10 is disposed on the flat surface 10B of the original 10. The number of protrusions 12 is not limited. The flat surface 10B may be a perfectly flat surface or may be a flat surface at first glance.

As illustrated in FIG. 1, in this embodiment, the protrusion 12 is constituted by a needle portion 12A which is tapered in the direction away from the flat surface 10B. The protrusion 12 is a so-called cone, and the cone includes a pyramid, a circular cone, and the like.

For example, the protrusion 12 preferably has a height of 100 to 2000 μm from the flat surface 10B of the original 10 and has a tip diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

The inclined portion 10C is formed in an enclosed shape on the outer peripheral portion of the protruding pattern 10A formed at the center portion on the flat surface 10B and gradually increases in thickness from the inside (the center side of the flat surface 10B) toward the outside (the end portion side of the flat surface 10B).

The thickness of the inclined portion 10C can be referred to as the height of the inclined portion 10C.

Figure 2B:
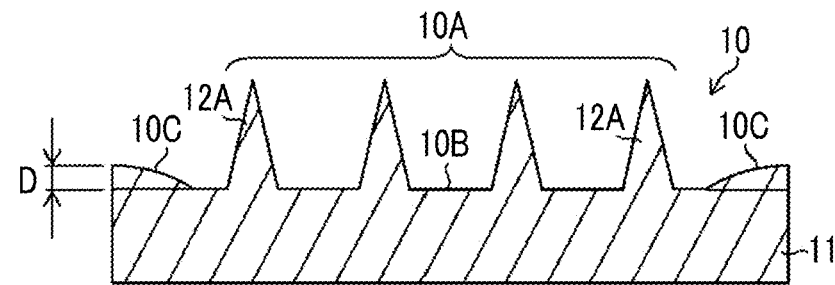
FIG. 2B is a vertical sectional view of the original having an arcuate inclined portion.

FIGS. 2A and 2B show two preferable embodiments in which the thickness of the inclined portion 10C gradually increases.

The inclined portion 10C in FIG. 2A has a vertical sectional shape formed in a right-angled triangle such that the thickness thereof linearly increases from the inside (the center portion side) toward the outside (the periphery portion side) of the flat surface 10B (hereinafter, referred to as a linear inclined portion). Furthermore, the inclined portion 10C in FIG. 2B has a vertical sectional shape formed in an arcuate shape such that the thickness thereof increases in an arc shape from the inside toward the outside of the flag surface 10B and thereafter the increase in thickness gradually decreases, that is, the thickness increases so-called arcuately (hereinafter, referred to as an arcuate inclined portion). The term "a vertical sectional shape formed in an arcuate shape" means, when a horizontal oval shape is divided into four equal parts by a vertical line and a horizontal line passing through the center, the sectional shape of one divided part.

(Second Embodiment of Original)

Figure 3A:
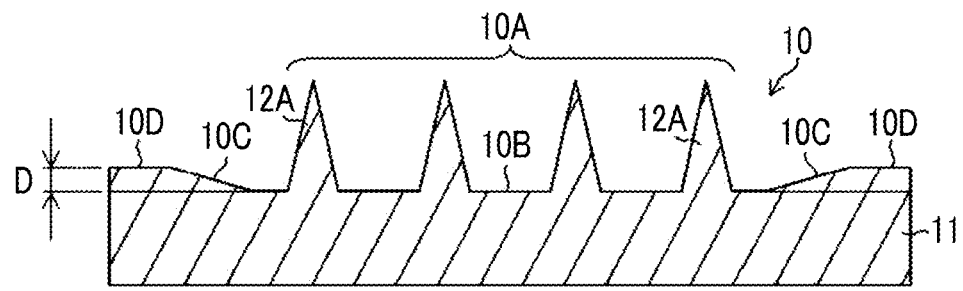
FIG. 3A is a vertical sectional view of the original having a flat portion which is formed to be connected to an inclination terminal of the linear inclined portion.
Figure 3B:
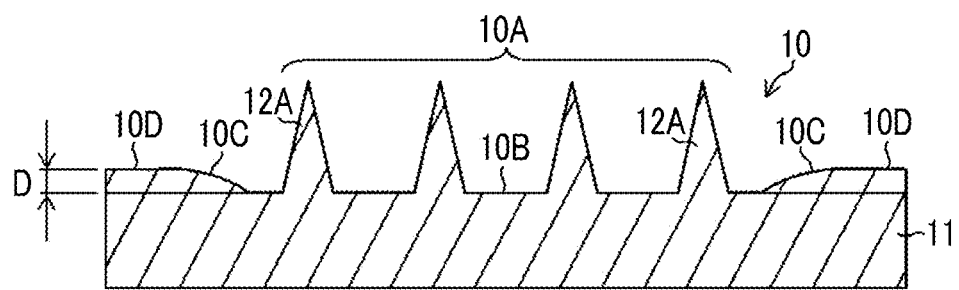
FIG. 3B is a vertical sectional view of the original having the flat portion which is formed to be connected to the inclination terminal of the arcuate inclined portion.

FIGS. 3A and 3B are perspective views illustrating a second embodiment of the original 10 of the present invention.

The second embodiment of the original 10 includes the protruding pattern 10A formed at the center portion on one flat surface 10B of the base 11, the inclined portion 10C formed on the outer peripheral portion of the protruding pattern 10A, and a flat portion 10D which is formed to be connected to the inclination terminal of the inclined portion 10C.

Here, the inclination terminal refers to a terminal where the thickness of the inclined portion 10C gradually increases to the maximum thickness D and the inclination ends. Therefore, the flat portion 10D is formed to have the same thickness as the maximum thickness D of the inclined portion 10C.

The original 10 in FIG. 3A refers to a case where the flat portion 10D is formed to be connected to the inclination terminal of the linear inclined portion 10C. The original 10 in FIG. 3B refers to a case where the flat portion 10D is formed to be connected to the inclination terminal of the arcuate inclined portion 10C. The protruding pattern 10A of the original 10 is the same as the protruding pattern 10A of the first embodiment.

(Method of Setting Maximum Thickness of Inclined Portion of Original)

The maximum thickness D of the inclined portion 10C of the original 10 is set as follows.

Since the case of the linear inclined portion 10C (FIG. 2A), the case of the arcuate inclined portion 10C (FIG. 2B), the case where the flat portion 10D connected to the inclination terminal of the linear inclined portion 10C is provided (FIG. 3A), and the case where the flat portion 10D connected to the inclination terminal of the arcuate inclined portion 10C is provided (FIG. 3B) have the same method of setting the maximum thickness D of the inclined portion 10C, the case of the linear inclined portion 10C will now be described as an example.

Figure 4A:
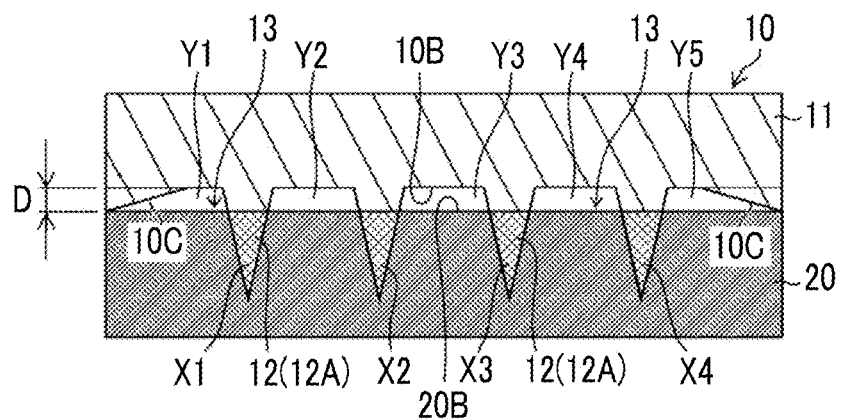
FIG. 4A is an explanatory view illustrating a method of setting a maximum thickness D of an inclined portion of the original.

FIG. 4A is a vertical sectional view illustrating the original 10 which is pressed against a surface 20B side of a thermoplastic resin sheet 20 such that the plurality of protrusions 12 (12A) of the protruding pattern 10A are pushed into the thermoplastic resin sheet 20 until the part of the linear inclined portion 10C having the maximum thickness D comes into close contact with the surface 20B of the thermoplastic resin sheet 20.

The original 10 is an example in which a total of 16 protrusions 12 (12A) are arranged in a two-dimensional array of 4 rows and 4 columns in the protruding pattern 10A, and the inclined portion 10C is formed in an enclosed shape the outer peripheral portion of the protruding pattern 10A. FIG. 4A is a vertical sectional view of the protruding pattern 10A, and the protrusions 12 are also formed in the forward and rearward directions of FIG. 4A. In addition, FIG. 4A is a vertical sectional view conceptually illustrating the original 10, and FIG. 4A and FIG. 1 are different from each other in the number of protrusions 12 constituting the protruding pattern 10A.

The maximum thickness D of the inclined portion 10C is set so that the total volume (X1+X2+X3+X4+ . . . +X16) of the parts (mesh parts in FIG. 4A) of the 16 protrusions 12 (12A) constituting the protruding pattern 10A, which are pushed into the thermoplastic resin sheet 20, is equal to the total volume (Y1+Y2+Y3+Y4+Y5+ . . . +Y25) of spaces 13 (white parts in FIG. 4A) enclosed by the flat surface 10B of the original 10, the surface 20B of the thermoplastic resin sheet 20, and the inclined portion 10C. In a case where a total of 16 protrusions 12 (12A) are arranged in a two-dimensional array of 4 rows and 4 columns as the protruding pattern 10A, 25 spaces 13 are formed.

Figure 4B:
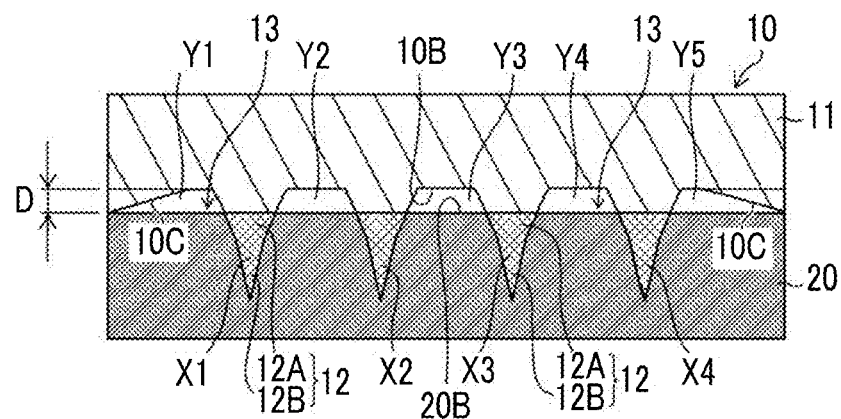
FIG. 4B is another explanatory view illustrating the method of setting the maximum thickness D of the inclined portion of the original.

FIG. 4B is a vertical sectional view illustrating the protruding pattern 10A, in which the shape of the protrusion 12 is constituted by the needle portion 12A and a frustum portion 12B, being pushed into the thermoplastic resin sheet 20 until the part of the linear inclined portion 10C having the maximum thickness D comes into close contact with the surface 20B of the thermoplastic resin sheet 20. FIG. 4B refers to a case where the needle portion 12A and a part of the frustum portion 12B are pushed into the thermoplastic resin sheet 20.

Even in this case, the maximum thickness D of the inclined portion 10C is set so that the total volume (X1+X2+X3+X4+ . . . +X16) of the parts (mesh parts in FIG. 4B) pushed into the thermoplastic resin sheet 20 is equal to the total volume (Y1+Y2+Y3+Y4+Y5+ . . . +Y25) of the spaces 13 (white parts in FIG. 4B) enclosed by the flat surface 10B of the original 10, the surface 20B of the thermoplastic resin sheet 20, and the inclined portion 10C.

That is, the maximum thickness D of the inclined portion 10C is set so that all the raised parts on the surface 20B of the thermoplastic resin sheet 20 corresponding to the total volume (X1+X2+X3+X4+ . . . +X16) of the pushed parts of the protruding pattern 10A can be accommodated in the total volume (Y1+Y2+Y3+Y4+Y5+ . . . +Y25) of the spaces 13, regardless of the shape (linear shape, or arcuate shape) of the inclined portion 10C, the presence or absence of the flat portion 10D, and the shape of the protrusion 12.

[Embodiment of Production Method of Mold] An embodiment of a production method of a mold of the present invention using the above-described original 10 will be described using the original 10 having the linear inclined portion 10C in FIG. 2A as an example.

FIGS. 5A to 5D are process diagrams illustrating a procedure of the production method of a mold.

Figure 5A:
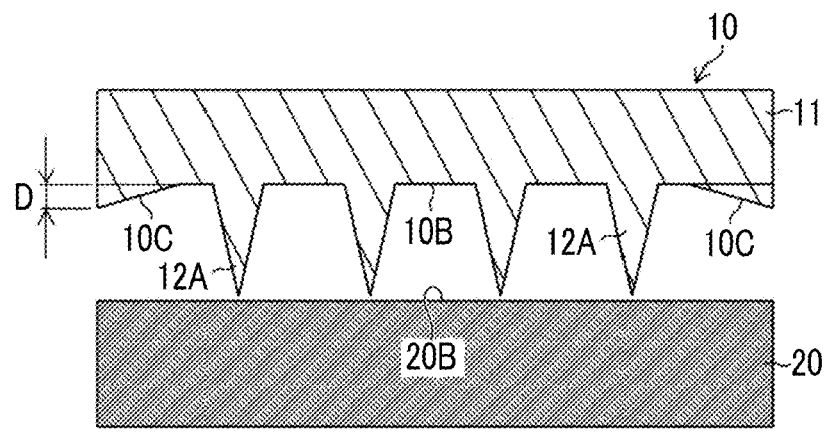
FIG. 5A is a vertical sectional view illustrating the preparation of the original and a thermoplastic resin sheet in a production method of a mold.

FIG. 5A illustrates a preparation process of preparing the original 10, and the thermoplastic resin sheet 20 which is the material of the mold.

The thermoplastic resin sheet 20 is set, for example, on a table (not illustrated). The thermoplastic resin sheet 20 has a thickness of 0.5 to 2.0 mm, for example, and has the surface 20B. A recessed pattern, which will be described later, is formed on the surface 20B side. It is preferable that the thickness of the thermoplastic resin sheet 20 is equal to or greater than at least the height of the protrusion 12 of the original 10.

The thermoplastic resin forming the thermoplastic resin sheet 20 is not particularly limited. For example, polyethylene terephthalate, polycarbonate, polymethyl methacrylate, polystyrene, polyethylene, a liquid crystal polymer, and polylactic acid may be suitably used.

The thermoplastic resin sheet 20 means a thermoplastic resin in a state of having a small film thickness and a self-supporting property at room temperature. "Self-supporting property" means that a single body can hold its form without the support of other members.

Figure 5B:
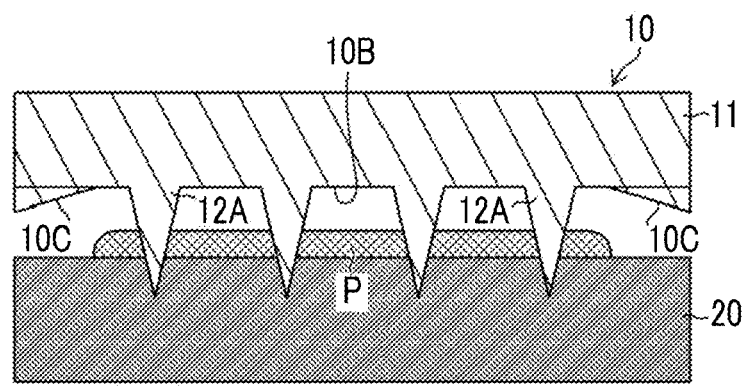
FIG. 5B is a vertical sectional view of the original which is pressed against the thermoplastic resin sheet up to the middle of the original in the production method of a mold.
Figure 5C:
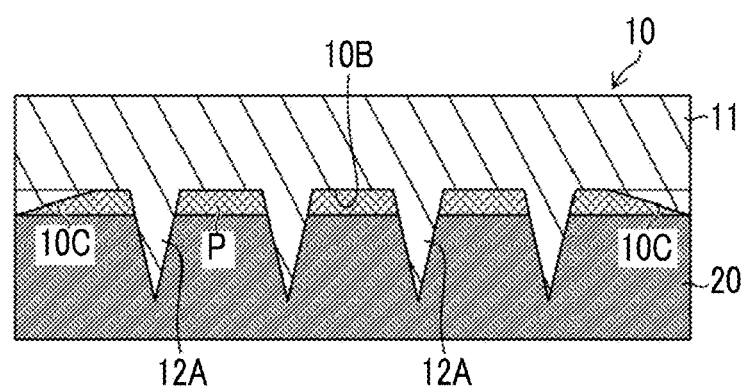
FIG. 5C is a vertical sectional view of the original which is pressed against the thermoplastic resin sheet until the original and the thermoplastic resin sheet are brought into close contact with each other in the production method of a mold.
Figure 5D:
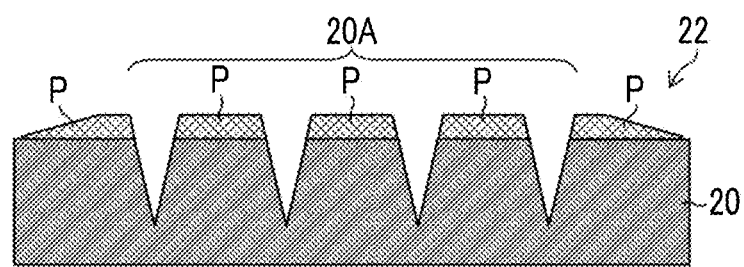
FIG. 5D is a vertical sectional view of a mold formed in the production method of a mold.

FIGS. 5B to 5D show a forming process of forming a recessed pattern 20A on the thermoplastic resin sheet 20 by pressing the original 10 against the surface 20B side of the thermoplastic resin sheet 20, and thereafter cooling and peeling the original 10.

As illustrated in FIG. 5B, the original 10 which is heated is pressed against the surface 20B side of the thermoplastic resin sheet 20. The original 10 is heated to a temperature at which the thermoplastic resin sheet 20 is softened. Heating is performed by a heater (not illustrated). The original 10 is heated to an appropriate temperature depending on the thermoplastic resin forming the thermoplastic resin sheet 20.

Accordingly, the protruding pattern 10A of the original 10 is pushed into the thermoplastic resin sheet 20. FIG. 5B is a view illustrating the protrusions 12 constituting the protruding pattern 10A of the original 10, which are pushed into the thermoplastic resin sheet 20 up to the middle of the protrusions 12. By pushing the protruding pattern 10A, the surface 20B of the thermoplastic resin sheet 20 is raised by the volume corresponding to the total volume of the pushed parts of the protrusions 12 (12A), such that raised portions P are formed.

In FIGS. 5B to 5D, the thermoplastic resin sheet 20 is indicated by diagonal lines and the raised portions P are indicated by meshes. However, this is for clearly indicating the raised portions P, and there is no distinction therebetween in appearance.

As illustrated in FIG. 5C, the original 10 which is further heated is pressed against the surface 20B of the thermoplastic resin sheet 20, and the protruding pattern 10A is pushed into the thermoplastic resin sheet 20 until the inclined portion 10C of the original 10 comes into close contact with the surface 20B of the thermoplastic resin sheet 20.

In addition, while pressing the heated original 10, the side of the surface 20B of the thermoplastic resin sheet 20 is heated for a certain period of time.

By pushing the protruding pattern 10A, the surface 20B of the thermoplastic resin sheet 20 is further raised and fills all the spaces 13 described above. The total volume of the spaces 13 is adjusted by the sizes of the raised portions P on the surface 20B of the thermoplastic resin sheet 20, that is, the total volume of the pushed parts of the protruding pattern 10A and the maximum thickness D of the inclined portion 10C.

Next, in the state in which the original 10 is pressed against the thermoplastic resin sheet 20, the original 10 is cooled until the thermoplastic resin sheet 20 is cooled to the softening temperature or lower.

Last, as illustrated in FIG. 5D, the original 10 and the thermoplastic resin sheet 20 are peeled away from each other, thereby forming the recessed pattern 20A having the inverted shape of the protruding pattern 10A on the surface 20B side of the thermoplastic resin sheet 20. Accordingly, a mold 22 is produced.

The recessed pattern 20A refers to a state in which recesses extending from the surface 20B of the thermoplastic resin sheet 20 toward the other surface are disposed on the surface 20B side of the thermoplastic resin sheet 20. The number of recesses, the arrangement of the recesses, the depth of the recesses, and the like are not limited. Since the recessed pattern 20A is the inverted shape of the protruding pattern 10A, the size, number, and arrangement of the recesses of the recessed pattern 20A are basically the same as those of the protrusions 12 pushed into the thermoplastic resin sheet 20.

As described above, as the protruding pattern 10A of the original 10 presses the thermoplastic resin sheet 20, the surface of the thermoplastic resin sheet 20 is raised.

Figure 6A:
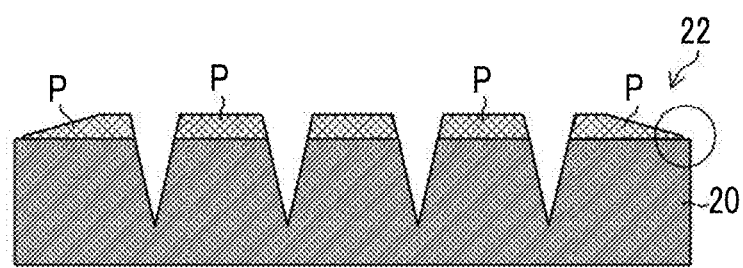
FIG. 6A is a sectional view illustrating an end portion of the mold produced by using the original having the inclined portion.
Figure 6B:
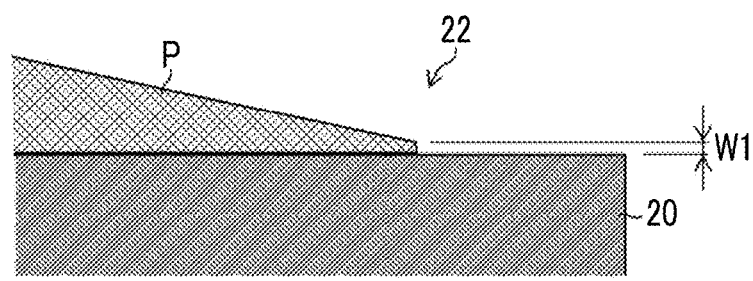
FIG. 6B is an enlarged sectional view of a part indicated by the circled in FIG. 6A.

However, as illustrated in the enlarged view of the produced mold 22 in FIG. 6A and the end portion (a part enclosed by the circle in FIG. 6A) of the recessed pattern 20A in FIG. 6B, the raised portion P of the end portion of the thermoplastic resin sheet 20 corresponding to the inclined portion 10C of the original 10 decreases in thickness from the inside toward the outside. Accordingly, the generation of a stepped portion at the end portion (peripheral portion) of the recessed pattern 20A of the produced mold 22 can be prevented. Even if a stepped portion is formed, as illustrated in FIG. 6B, the stepped portion height W1 can be made extremely small.

Figure 6C:
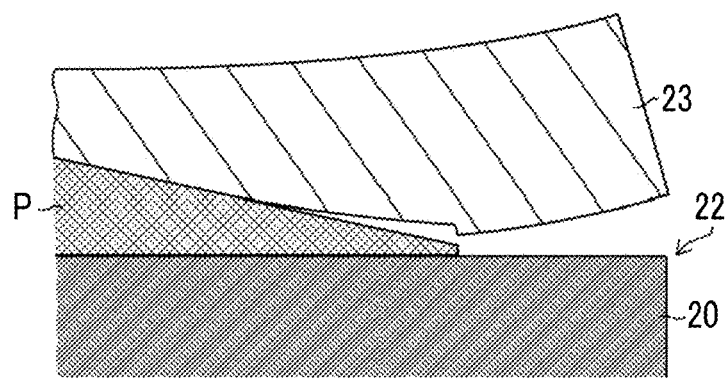
FIG. 6C is a view illustrating peeling a duplicate product from the mold.

Therefore, as illustrated in FIG. 6C, the mold 22 produced by the production method of the mold of this embodiment does not cause the stepped portion to become peeling resistance when a duplicate mold 23 (or formed product) is peeled away from the mold 22 in the process of producing the duplicate mold 23 (or formed product). Accordingly, the duplicate mold 23 (or formed product) can be easily peeled away from the mold 22, and peeling failure such as breaking of the duplicate mold 23 (or formed product) at the stepped portion during peeling can be prevented.

Moreover, since the inclined portion 10C is provided in the original 10, releasability of the original 10 itself can be improved when the mold 22 is produced from the original 10.

Figure 7A:
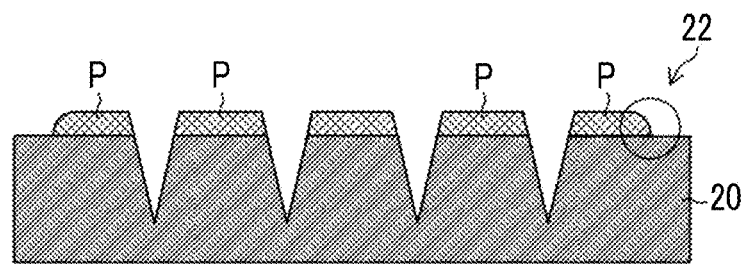
FIG. 7A is a sectional view illustrating an end portion of a mold produced by using an original without an inclined portion.
Figure 7B:
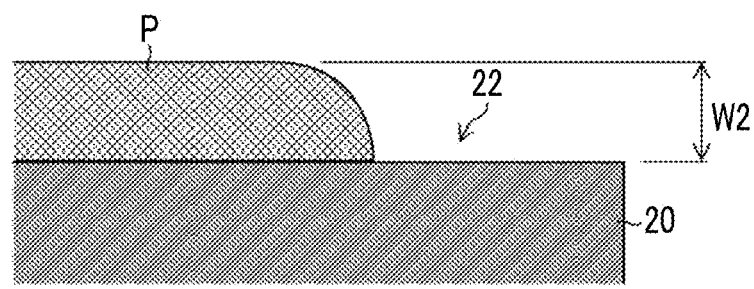
FIG. 7B is an enlarged sectional view of a part indicated by the circled in FIG. 7A.
Figure 7C:
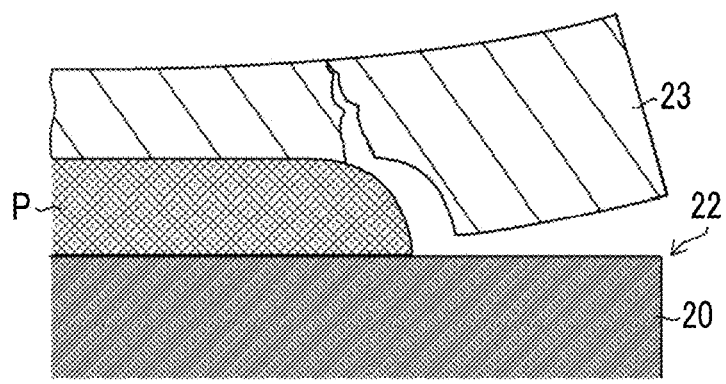
FIG. 7C is a view illustrating peeling the duplicate product from the mold.

Contrary to this, FIGS. 7A to 7C refer to a case where the duplicate mold 23 (formed product) is produced using the mold 22 produced using the original 10 without the inclined portion 10C.

As illustrated in the enlarged view of the produced mold 22 in FIG. 7A and the end portion (a part enclosed by the circle in FIG. 7A) of the recessed pattern 20A in FIG. 7B, the raised portion P ends while the raised portion P of the end portion of the thermoplastic resin sheet 20 does not decrease in thickness from the inside toward the outside and maintains the same thickness. Accordingly, a stepped portion at a substantially right angle is formed at the end position of the raised portion P, that is, the end portion (peripheral portion) of the recessed pattern 20A. As illustrated in FIG. 7B, the stepped portion height W2 of the stepped portion at a substantially right angle, which is formed on the end portion (peripheral part) of the recessed pattern 20A is significantly larger than the stepped portion height W1 in the case where the inclined portion 10C illustrated in FIG. 7B is provided.

Therefore, as illustrated in FIG. 7C, the mold 22 produced using the original 10 without the inclined portion 10C causes the stepped portion to become resistance when the duplicate mold 23 (or formed product) is peeled away from the mold 22 in the process of producing the duplicate mold 23 (or formed product) such that the duplicate mold 23 (or formed product) cannot be easily peeled away and peeling failure such as breaking at the stepped portion is more likely to occur.

Figure 8A:
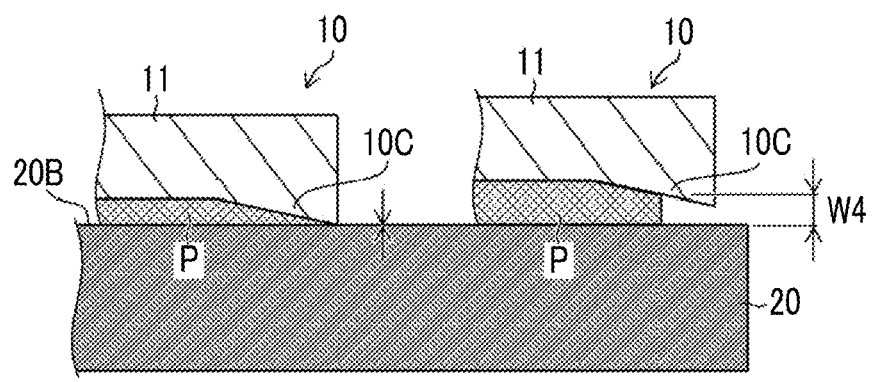
FIG. 8A is a partial sectional view of a case where the linear inclined portion is in close contact with the surface of the thermoplastic resin sheet and a case where the linear inclined portion and the surface of the thermoplastic resin sheet are not in close contact with each other.
Figure 8B:
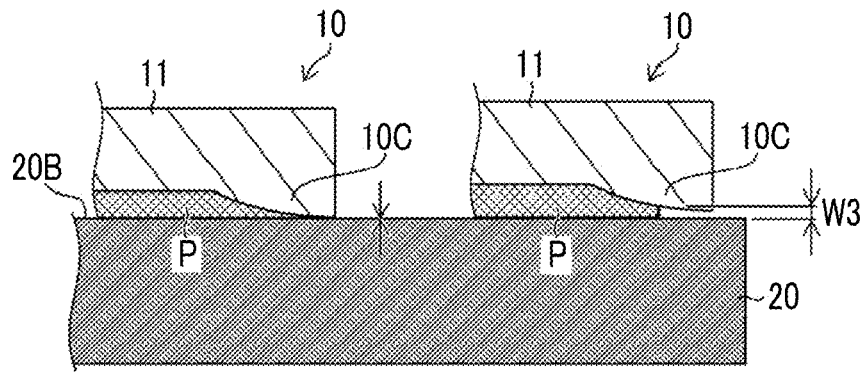
FIG. 8B is a partial sectional view of a case where the arcuate inclined portion is in close contact with the surface of the thermoplastic resin sheet and a case where the arcuate inclined portion and the surface of the thermoplastic resin sheet are not in close contact with each other.

FIGS. 8A and 8B are views for comparison between the linear inclined portion 10C and the arcuate inclined portion 10C of the original 10 illustrated in FIGS. 2A and 2B in the raised portion P formed on the end portion of the recessed pattern 20A of the surface 20B of the thermoplastic resin sheet 20. In FIGS. 8A and 8B, only the part of the inclined portion 10C of the original 10 and the part of the thermoplastic resin sheet 20 corresponding to the inclined portion 10C are illustrated.

FIG. 8A refers to the case of the linear inclined portion 10C, the left figure of FIG. 8A is a view when the inclined portion 10C of the original 10 and the surface 20B of the thermoplastic resin sheet 20 are brought into close contact with each other by pressing, and the right figure is a view when the inclined portion 10C and the surface 20B are not in close contact with each other. FIG. 8B refers to the case of the arcuate inclined portion 10C, the left figure of FIG. 8B is a view when the inclined portion 10C of the original 10 and the surface 20B of the thermoplastic resin sheet 20 are brought into close contact with each other by pressing, and the right figure is a view when the inclined portion 10C and the surface 20B are not in close contact with each other.

As can be seen from the left figure of FIG. 8A and the left figure of FIG. 8B, in the case where the inclined portion 10C of the original 10 and the surface 20B of the thermoplastic resin sheet 20 are in close contact with each other, a stepped portion is not formed in the linear inclined portion 10C or the arcuate inclined portion 10C. Contrary to this, as can be seen from the right figure of FIG. 8A and the right figure of FIG. 8B, in the case where the inclined portion 10C of the original 10 and the surface 20B of the thermoplastic resin sheet 20 are not in close contact with each other, the stepped portion height W3 formed by the arcuate inclined portion 10C is smaller than the stepped portion height W4 formed by the linear inclined portion 10C.

However, the stepped portion height W4 formed by the linear inclined portion 10C is smaller than the stepped portion height W2 in the case where the inclined portion 10C illustrated in FIG. 7B is absent.

As a factor that causes the inclined portion 10C of the original 10 and the surface 20B of the thermoplastic resin sheet 20 not to come into close contact with each other, there is a case where the pressing stroke of the original 10 against the thermoplastic resin sheet 20 is unstable. In addition, there is a case where the thermoplastic resin sheet 20 is less likely to soften and the resin raised from the surface 20B of the thermoplastic resin sheet 20 is less likely to spread on the surface 20B. Therefore, in such cases, it is more preferable to use the original 10 having the arcuate inclined portion 10C.

Figure 9A:
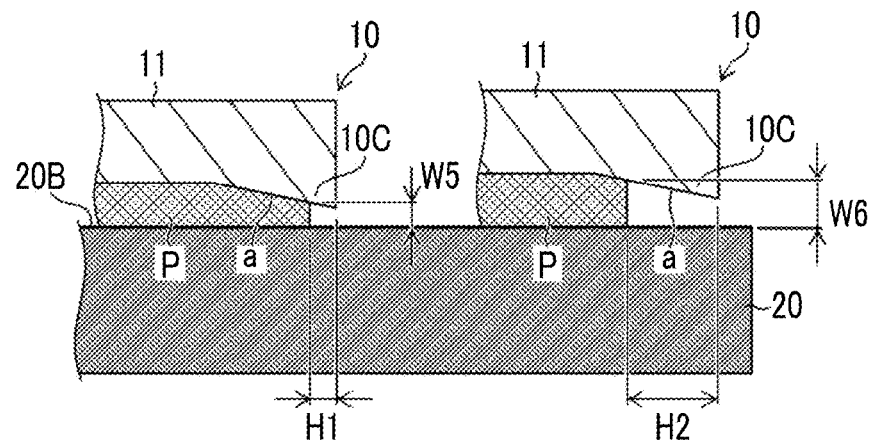
FIG. 9A is a partial sectional view of a case where a flat portion which is formed to be connected to the inclination terminal of the linear inclined portion is absent.
Figure 9B:
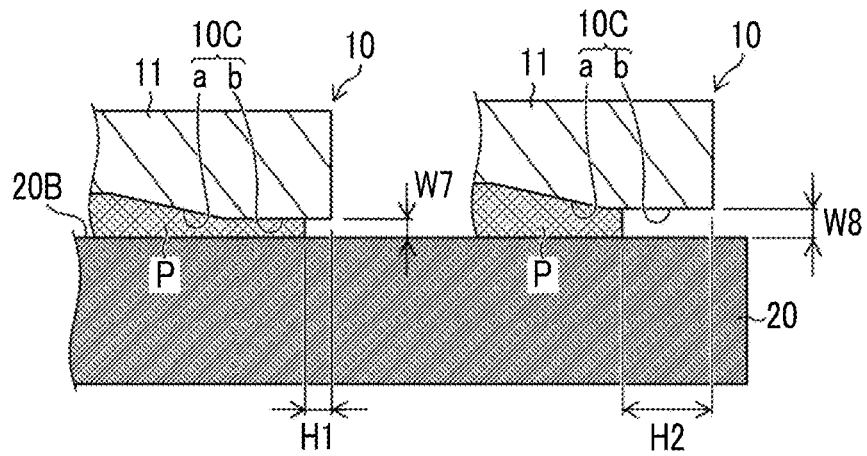
FIG. 9B is a partial sectional view of a case where the flat portion which is formed to be connected to the inclination terminal of the linear inclined portion is present.

FIGS. 9A and 9B view for comparison between the case where the flat portion 10D is absent at the inclination terminal of the linear inclined portion 10C (FIG. 9A) and the case where the flat portion 10D is present (FIG. 9B) in the raised portion P formed on the end portion of the recessed pattern 20A of the surface 20B of the thermoplastic resin sheet 20. In FIGS. 9A and 9B, only the part of the inclined portion 10C of the original 10 and the part of the thermoplastic resin sheet 20 corresponding to the inclined portion 10C are illustrated.

As can be seen from the left figure of FIG. 9A and the left figure of FIG. 9B, in a case where the raised portion P on the surface 20B of the thermoplastic resin sheet 20 spreads to a position H1 close to the inclination terminal of the inclined portion 10C of the original 10, the stepped portion height W7 in the case where the flat portion 10D is present is slightly smaller than the stepped portion height W5 in the case where the flat portion 10D is absent, and there is no significant difference therebetween.

Contrary to this, as can be seen from the right figure of FIG. 9A and the right figure of FIG. 9B, in a case where the raised portion P on the surface 20B of the thermoplastic resin sheet 20 does not spread to a position H2 distant from the inclination terminal of the inclined portion 10C of the original 10, the stepped portion height W8 in the case where the flat portion 10D is present is significantly smaller than the stepped portion height W6 in the case where the flat portion 10D is absent.

That is, in the case where the thermoplastic resin sheet 20 is less likely to soften and the resin raised from the surface 20B of the thermoplastic resin sheet 20 is less likely to spread on the surface 20B, by providing the flat portion 10D at the inclination terminal of the inclined portion 10C, the stepped portion height can be further reduced.

Next, a control method when the original 10 is pressed against the thermoplastic resin sheet 20 will be described.

Figure 10:
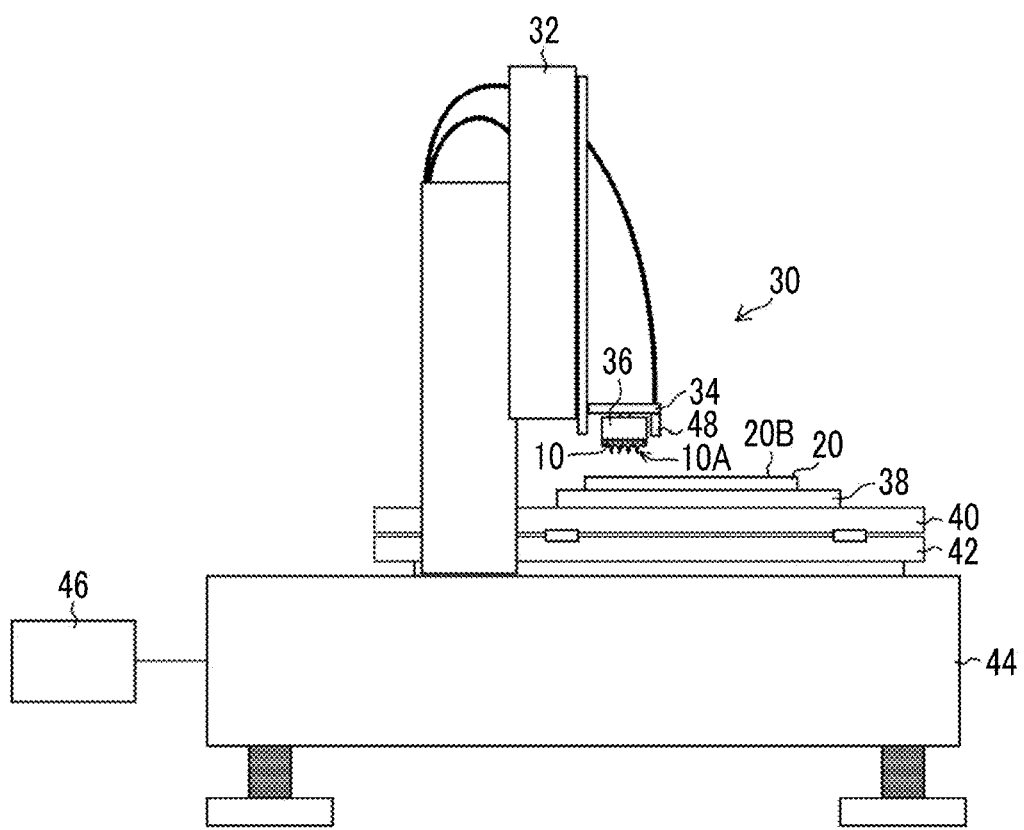
FIG. 10 is a configuration diagram illustrating the overall configuration of a pressing apparatus.

FIG. 10 is a schematic configuration diagram illustrating an example of a pressing apparatus 30 having an alignment function. As illustrated in FIG. 10, the pressing apparatus 30 includes a Z-axis drive mechanism 32 which drives the original 10 in a Z-axis direction, a connection portion 34 connected to the Z-axis drive mechanism 32, a holding portion 36 attached to the connection portion 34, a table 38 which supports the thermoplastic resin sheet 20, an X-axis drive mechanism 40 which drives the table 38 in an X-axis direction, a Y-axis drive mechanism 42 which drives the table 38 in a Y-axis direction, a stand 44, a control system 46, and a laser displacement meter 48. In addition, the original 10 is held by the holding portion 36, for example, by adsorption.

According to a first control method, in a case where alignment between the original 10 and the pressing position of the thermoplastic resin sheet 20 is necessary as in a case where the original 10 is pressed against a plurality of points of the thermoplastic resin sheet 20, first, the X-axis drive mechanism 40 and the Y-axis drive mechanism 42 are driven to align the original 10 and the thermoplastic resin sheet 20 with each other. In addition, when the heated original 10 is pressed against the thermoplastic resin sheet 20, the position of the surface 20B of the thermoplastic resin sheet 20 is measured. That is, before moving the original 10 in the pressing direction, for example, the control system 46 measures the distance between the protruding pattern 10A of the original 10 and the surface 20B of the thermoplastic resin sheet 20 by using the laser displacement meter 48. By measuring the distance, the position of the surface 20B of the thermoplastic resin sheet 20 can be detected.

On the basis of the measured distance, the control system 46 determines the amount of the protruding pattern 10A pushed from the position of the surface 20B of the thermoplastic resin sheet 20. The control system 46 drives the Z-axis drive mechanism 32, and the Z-axis drive mechanism 32 moves the original 10 to the position of the surface 20B of the thermoplastic resin sheet 20 and further pushes the original 10 toward the thermoplastic resin sheet 20 side by a certain amount (the pushing amount determined). Accordingly, the protruding pattern 10A is pushed into the thermoplastic resin sheet 20 up to the set pushing position of the protruding pattern 10A, and thus the inclined portion 10C of the original 10 and the surface 20B of the thermoplastic resin sheet 20 are brought into close contact with each other.

According to a second control method, in a case where the alignment described above is necessary, the X-axis drive mechanism 40 and the Y-axis drive mechanism 42 are first driven to align the original 10 and the thermoplastic resin sheet 20 with each other. The control system 46 drives the Z-axis drive mechanism 32, and the Z-axis drive mechanism 32 moves the original 10 to the position of the surface 20B of the thermoplastic resin sheet 20. The pressure applied to the original 10 is measured while the original 10 is moved by the Z-axis drive mechanism 32. The pressure measurement method is not particularly limited. For example, a load cell may be disposed between the original 10 and the holding portion 36, and the pressure applied to the original 10 may be measured by the load cell. The load cell is a measuring instrument that can measure a compressive force in the thickness direction thereof.

The control system 46 compares the measured pressure with a preset pressure. When the measured pressure reaches the preset pressure, the control system 46 determines that the protruding pattern 10A has reached the surface 20B of the thermoplastic resin sheet 20.

The control system 46 determines the amount of the protruding pattern 10A pushed from the position of the surface 20B of the thermoplastic resin sheet 20. The control system 46 drives the Z-axis drive mechanism 32 to push the original 10 toward the thermoplastic resin sheet 20 by a certain amount (the pushing amount determined). Accordingly, the protruding pattern 10A is pushed into the thermoplastic resin sheet 20 up to the set pushing position of the protruding pattern 10A, and thus the inclined portion 10C of the original 10 and the surface 20B of the thermoplastic resin sheet 20 are brought into close contact with each other.

According to a third control method, in a case where the alignment described above is necessary, the X-axis drive mechanism 40 and the Y-axis drive mechanism 42 are first driven to align the original 10 and the thermoplastic resin sheet 20 with each other. The control system 46 drives the Z-axis drive mechanism 32, and the Z-axis drive mechanism 32 moves the original 10 to the position of the surface 20B of the thermoplastic resin sheet 20. The pressure applied to the original 10 is measured while the original 10 is moved by the Z-axis drive mechanism 32.

The control system 46 compares the measured pressure with a preset pressure. In the third control method, the relationship between the pressure applied to the original 10 and the amount (depth) of the protruding pattern 10A pushed into the thermoplastic resin sheet 20 is previously obtained.

The control system 46 compares the measured pressure with a preset pressure. When the measured pressure reaches the set pressure, the control system 46 determines that the protruding pattern 10A has reached a desired pushing amount from the surface 20B of the thermoplastic resin sheet 20. In this embodiment, the control system 46 calculates the pushing amount from the previously obtained relationship based on the measured pressure.

In a case where the pushing amount calculated from the pressure is the desired pushing amount with respect to the thermoplastic resin sheet 20, the original 10 is not pushed into the thermoplastic resin sheet 20. That is, the control system 46 measures a pressure applied to the original 10, compares the measured pressure with a certain pressure value which is set, and determines the pushing amount of the original 10 as "0".

In a case where the pushing amount calculated from the pressure is smaller than the desired pushing amount with respect to the thermoplastic resin sheet 20, the control system 46 determines the amount of the protruding pattern 10A of the original 10 pushed into the thermoplastic resin sheet 20 based on the current position of the original 10. The control system 46 drives the Z-axis drive mechanism 32 to push the original 10 toward the thermoplastic resin sheet 20 by a certain amount (the pushing amount determined). Accordingly, the protruding pattern 10A is pushed into the thermoplastic resin sheet 20 up to the set pushing position of the protruding pattern 10A, and thus the inclined portion 10C of the original 10 and the surface 20B of the thermoplastic resin sheet 20 are brought into close contact with each other.

According to the above-described control methods, it becomes possible to push the original 10 into the thermoplastic resin sheet 20 with an accurate pressing stroke. In addition, the original 10 and the thermoplastic resin sheet 20 can be separated from each other by the above-described Z-axis drive mechanism 32.

Next, regarding the original 10 having the protruding pattern 10A and the inclined portion 10C, the original 10 having a different shape from that of the protrusions 12 constituting the protruding pattern 10A illustrated in FIG. 1 will be described.

Figure 11:
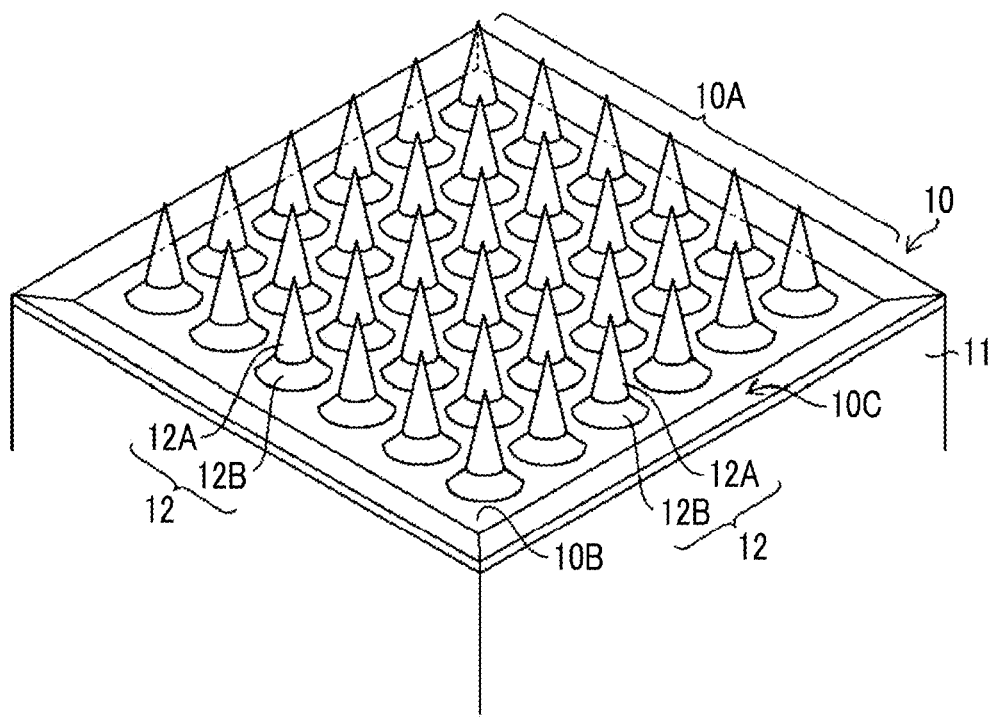
FIG. 11 is a perspective view of an original according to another aspect of the present invention, in which the original has protrusions different from those in FIG. 1.

FIG. 11 illustrates the original 10 in which the shape of the protrusion 12 is different from that in FIG. 1. The protrusion 12 included in the protruding pattern 10A illustrated in FIG. 11 is constituted by the frustum portion 12B and the needle portion 12A which is tapered in the direction away from one flat surface 10B of the base 11. The frustum portion 12B includes a square frustum, a circular cone frustum, and the like. Another frustum portion may be included between the frustum portion 12B and the needle portion 12A. In addition, the inclined portion 10C which is formed in an enclosed shape on the outer peripheral portion of the protruding pattern 10A and gradually increases in thickness from the inside toward the outside up to the set pushing position of the protruding pattern 10A is formed.

For example, the protrusion 12 preferably has a height of 100 to 2000 μm from the flat surface 10B of the original 10 and has a tip diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

The ratio of the height of the needle portion 12A to the height of the frustum portion 12B (the height of the needle portion 12A/the height of the frustum portion 12B) is preferably 1 to 10. The angle between the side surface of the frustum portion 12B and the flat surface 10B is preferably 10° to 60°.

Figure 12A:
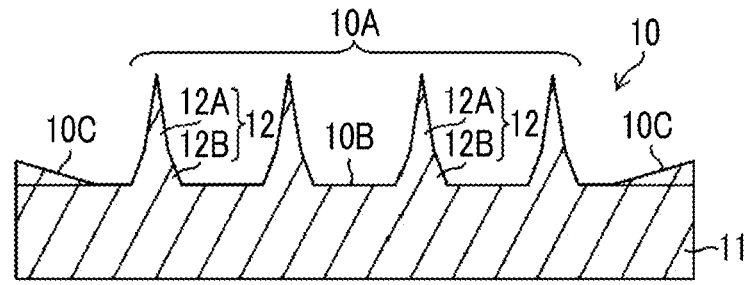
FIG. 12A is a sectional view of the original having the protrusions in FIG. 10 and having the linear inclined portion.
Figure 12B:
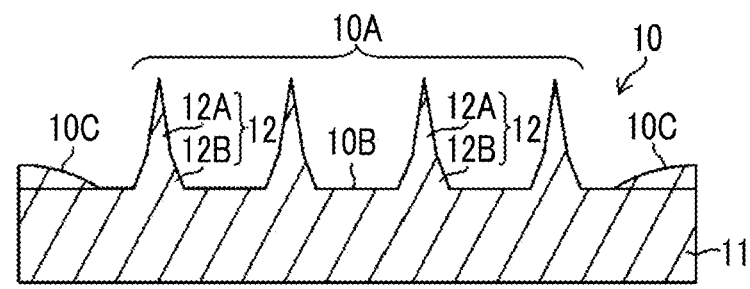
FIG. 12B is a sectional view of the original having the protrusions in FIG. 10 and having the arcuate inclined portion.

FIGS. 12A and 12B are vertical sectional views of the original 10 having the protrusions 12 in FIG. 11, FIG. 12A refers to a case where the linear inclined portion 10C is provided, and FIG. 12B refers to a case where the arcuate inclined portion 10C is provided. In addition, FIGS. 12A and 12B are conceptual views of the original 10, and FIGS. 12A and 12B and FIG. 11 are different from each other in the number of protrusions 12 constituting the protruding pattern 10A.

Furthermore, although not illustrated, the flat portion 10D as illustrated in FIG. 3A may be provided to be connected to the inclination terminal of the linear inclined portion 10C in FIG. 12A, and the flat portion 10D as illustrated in FIG. 3B may be provided to be connected to the inclination terminal of the arcuate inclined portion 10C in FIG. 12B.

Figure 13:
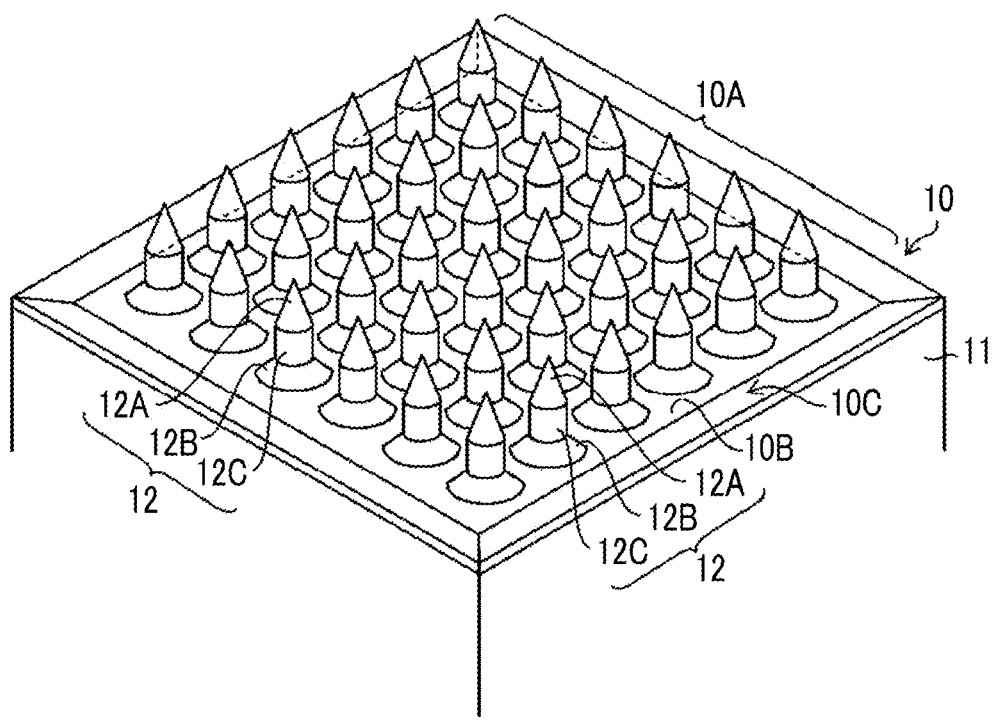
FIG. 13 is a perspective view of an original according to still another aspect of the present invention, in which the original has protrusions different from those in FIG. 1.

The protrusion 12 included in the protruding pattern 10A of the original 10 illustrated in FIG. 13 is constituted by the frustum portion 12B, a columnar portion 12C, and the needle portion 12A which is tapered in the direction away from the flat surface 10B. Here, the columnar portion 12C means a shape having two opposing parallel bottom surfaces, as represented by a cylinder or a rectangular parallelepiped, in which the areas of the two bottom surfaces are the same. In addition, an inclined portion which is formed in an enclosed shape on the outer peripheral portion of the protruding pattern 10A and gradually increases in thickness from the inside toward the outside up to the set pushing position of the protruding pattern 10A is formed.

For example, the protrusion 12 preferably has a height of 100 to 2000 μm from the flat surface 10B of the original 10 and has a tip diameter of Φ50 μm or less. In the case where a plurality of the protrusions 12 are provided, it is preferable that the interval between adjacent protrusions 12 is 300 to 2000 μm. It is preferable that the aspect ratio (the height of the protrusion/the width of the bottom surface of the protrusion) of the protrusion 12 is 1 to 5.

The ratio of the total height of the needle portion 12A and the columnar portion 12C to the height of the frustum portion 12B (the total height of the needle portion 12A and the columnar portion 12C/the height of the frustum portion 12B) is preferably 1 to 10. In addition, the ratio of the height of the needle portion 12A to the height of the columnar portion 12C (the height of the needle portion 12A/the height of the columnar portion 12C) is preferably 0.25 to 10. The angle between the side surface of the needle portion 12A and the flat surface 10B is preferably 45° to 85°. Furthermore, the angle between the side surface of the frustum portion 12B and the flat surface 10B is preferably 10° to 60°.

Figure 14A:
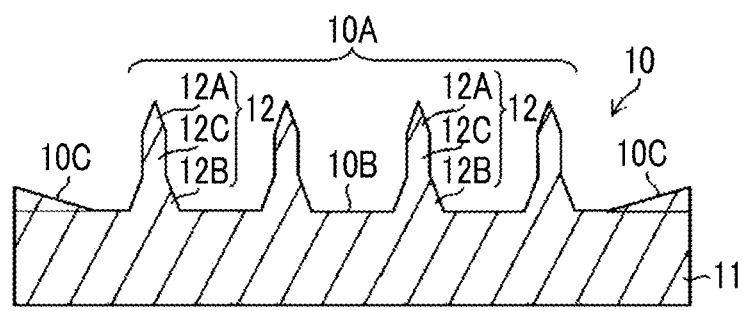
FIG. 14A is a sectional view of the original having the protrusions in FIG. 13 and having the linear inclined portion.
Figure 14B:
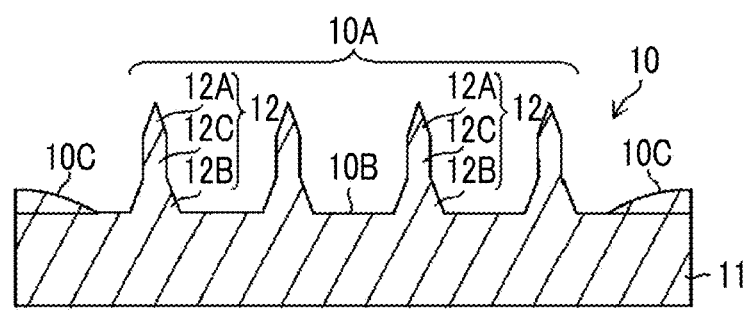
FIG. 14B is a sectional view of the original having the protrusions in FIG. 13 and having the arcuate inclined portion.

FIGS. 14A and 14B are vertical sectional views of the original 10 having the protrusions 12 in FIG. 13, FIG. 14A refers to a case where the linear inclined portion 10C is provided, and FIG. 14B refers to a case where the arcuate inclined portion 10C is provided. In addition, FIGS. 14A and 14B are conceptual views of the original 10, and FIGS. 14A and 14B and FIG. 13 are different from each other in the number of protrusions 12 constituting the protruding pattern 10A.

Furthermore, although not illustrated, the flat portion 10D as illustrated in FIG. 3A may be provided to be connected to the inclination terminal of the linear inclined portion 10C in FIG. 14A, and the flat portion 10D as illustrated in FIG. 3B may be provided to be connected to the inclination terminal of the arcuate inclined portion 10C in FIG. 14B.

FIGS. 15A to 15D show a process of producing the mold 22 using the original 10 having a combination of the protruding pattern 10A having the protrusions 12 constituted by the frustum portion 12B and the needle portion 12A in FIG. 11 and the arcuate inclined portion 10C.

Figure 15A:
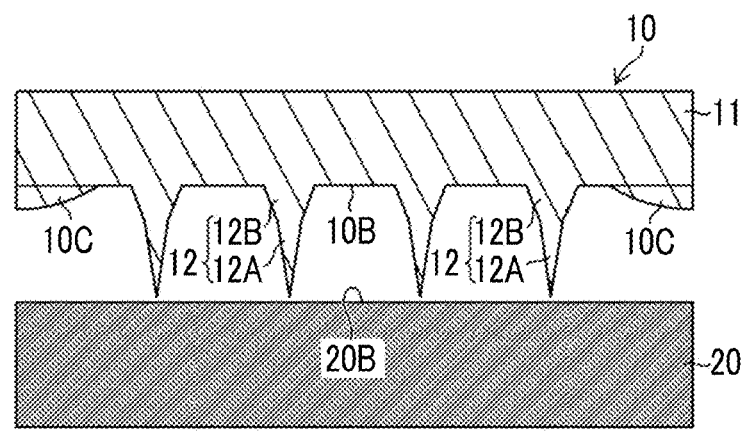
FIG. 15A is a sectional view illustrating preparation of the original in FIG. 12B and the thermoplastic resin sheet in the production method of a mold.

FIG. 15A is a preparation process of preparing the original 10 and the thermoplastic resin sheet 20.

Figure 15B:
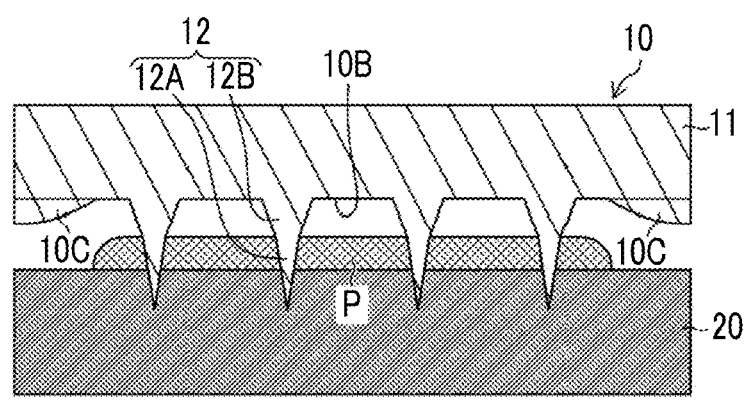
FIG. 15B is a sectional view of the original which is pressed against the thermoplastic resin sheet up to the middle of the original in the production method of a mold.
Figure 15C:
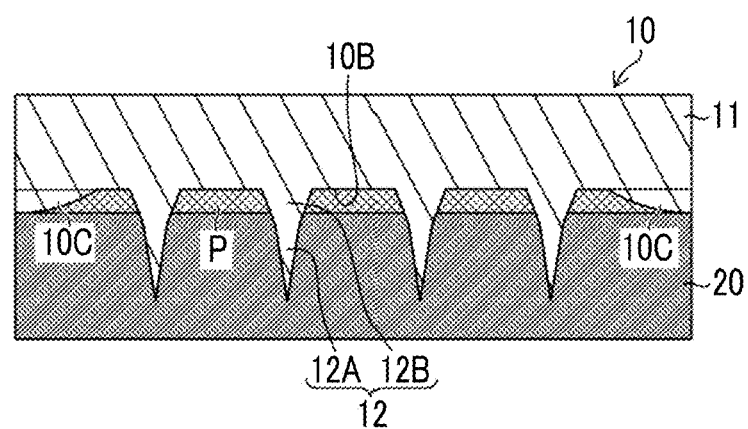
FIG. 15C is a sectional view of the original which is pressed against the thermoplastic resin sheet until the original and the thermoplastic resin sheet are brought into close contact with each other in the production method of a mold.
Figure 15D:
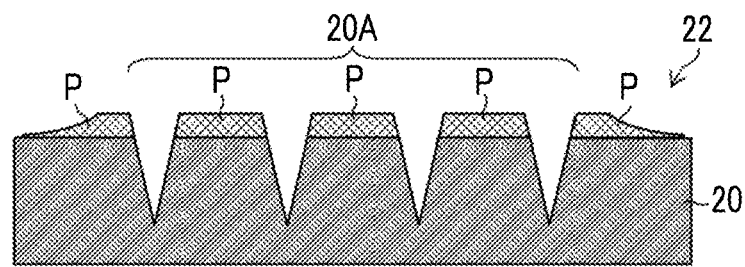
FIG. 15D is a sectional view of a mold formed in the production method of a mold.

FIGS. 15B to 15D show a forming process of forming the recessed pattern 20A on the thermoplastic resin sheet 20 by pressing the original 10 against the surface 20B side of the thermoplastic resin sheet 20, and thereafter cooling and peeling the original 10.

As illustrated in FIG. 15B, the original 10 which is heated is pressed against the surface 20B side of the thermoplastic resin sheet 20. Accordingly, the protruding pattern 10A of the original 10 is pressed against the thermoplastic resin sheet 20. FIG. 15B is a view illustrating the protrusions 12 constituting the protruding pattern 10A of the original 10, which are pushed into the thermoplastic resin sheet 20 up to the middle of the protrusions 12. By pushing the protruding pattern 10A, the surface 20B of the thermoplastic resin sheet 20 is raised by the volume corresponding to the total volume of the pushed parts of the protrusions 12, such that raised portions P are formed.

Next, as illustrated in FIG. 15C, the protruding pattern 10A is further pushed until the inclined portion 10C of the original 10 and the surface 20B of the thermoplastic resin sheet 20 are brought into close contact with each other. By pushing the protruding pattern 10A, the surface 20B of the thermoplastic resin sheet 20 is further raised and fills all the spaces 13 described above. At this time, since the shape of the protrusion 12 is constituted by the needle portion 12A and the frustum portion 12B, the raised portions P on the surface 20B of the thermoplastic resin sheet 20 receive a force spreading in the horizontal direction from the frustum portion 12B.

Accordingly, compared to the case where the shape of the protrusion 12 is constituted by only the needle portion 12A, the raised portions P are more likely to spread toward the inclination terminal of the inclined portion 10C provided in the original 10, thereby further preventing the generation of the stepped portion.

Next, in the state in which the original 10 is pressed against the thermoplastic resin sheet 20, the original 10 is cooled until the thermoplastic resin sheet 20 is cooled to the softening temperature or lower.

Last, as illustrated in FIG. 15D, the original 10 and the thermoplastic resin sheet 20 are separated from each other, thereby forming the recessed pattern 20A having the inverted shape of the protruding pattern 10A on the surface 20B side of the thermoplastic resin sheet 20. Accordingly, the mold 22 is produced.

[Production Method of Large Mold] Next, a process of producing the large mold 22 having a plurality of the recessed patterns 20A by pressing the original 10 having one protruding pattern 10A against a plurality of points on the surface 20B of the large thermoplastic resin sheet 20 will be described.

Figure 16A:
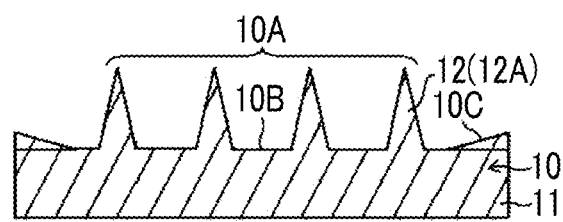
FIG. 16A is a sectional view illustrating preparation of an original in a production method of a large mold.

FIG. 16A illustrates a process of preparing the original 10, and an example in which the original 10 described with reference to FIG. 2A is used will be described. That is, the original 10 has one protruding pattern 10A formed at the center portion on one flat surface 10B and the linear inclined portion 10C formed on the outer peripheral portion of the protruding pattern 10A.

Figure 16B:
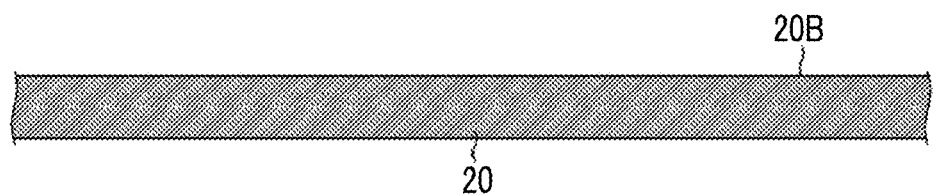
FIG. 16B is a sectional view illustrating preparation of a thermoplastic resin sheet in the production method of a large mold.

Next, FIG. 16B illustrates a preparation process of preparing the large thermoplastic resin sheet 20. The thermoplastic resin sheet 20 as the material of the mold 22 is prepared, and the thermoplastic resin sheet 20 is set, for example, on the table (not illustrated).

The large thermoplastic resin sheet 20 has a thickness of, for example, 0.5 to 2.0 mm and a size of 100×100 to 300×300, and has the surface 20B against which the protruding pattern 10A of the original 10 to be pressed. A plurality of recessed patterns 20A to be described later are formed on the surface 20B side.

Figure 16C:
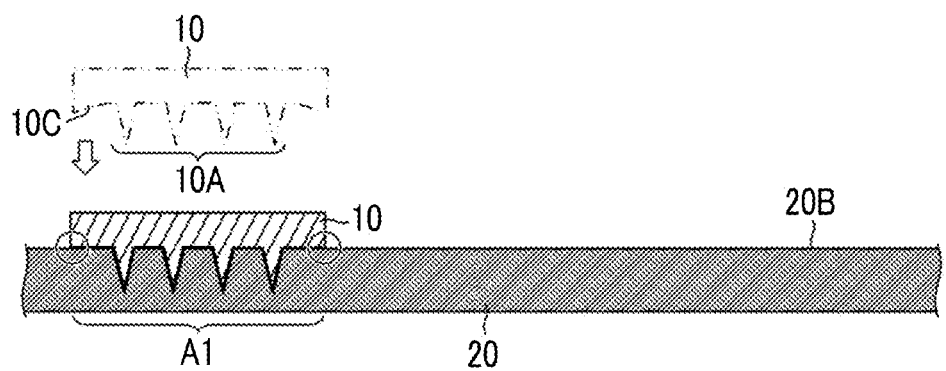
FIG. 16C is a sectional view illustrating the original which is pressed against a region of the thermoplastic resin sheet in the production method of a large mold.
Figure 16D:
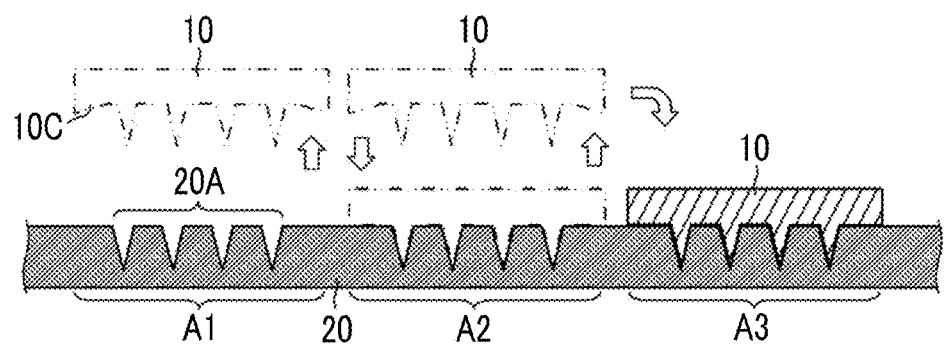
FIG. 16D is a sectional view illustrating the original which is pressed against another region of the thermoplastic resin sheet in the production method of a large mold.

FIGS. 16C and 16D show an alignment process, the forming process of forming the recessed pattern 20A, the alignment process and the forming process which are repeatedly performed.

First, a position (for example, a region A1) at which the original 10 is pressed against the thermoplastic resin sheet 20 is determined by moving the prepared original 10 and the thermoplastic resin sheet 20 relative to each other. For the alignment, the pressing apparatus 30 having the alignment function illustrated in FIG. 10 may be used. That is, the alignment is performed by moving the table 38 that supports the thermoplastic resin sheet 20 using the X-axis drive mechanism 40 and the Y-axis drive mechanism 42 which move in directions perpendicular to each other on the horizontal plane.

For accurate alignment, for example, it is preferable to provide alignment marks for alignment on the surface 20B of the thermoplastic resin sheet 20. Furthermore, in order to detect the original 10, the thermoplastic resin sheet 20, and the alignment marks, it is preferable to provide an imaging device or the like.

Next, the heated original 10 is pressed against the surface 20B side of the thermoplastic resin sheet 20 by the Z-axis drive mechanism 32 of the pressing apparatus 30. By the pressing, the protruding pattern 10A of the original 10 is pressed against the thermoplastic resin sheet 20, and the surface 20B of the thermoplastic resin sheet 20 is raised.

However, since the inclined portion 10C is formed on the original 10, the raised portion of the surface 20B of the thermoplastic resin sheet 20 corresponding to the inclined portion 10C of the original 10 decreases in thickness from the inside toward the outside. In addition, in FIGS. 16C to 16E, although the raised portion P is strictly present, the illustration thereof is omitted here.

Accordingly, the generation of the stepped portion at the end portion of the surface 20B of the thermoplastic resin sheet 20 (a part indicated by the circle in FIG. 16C) can be prevented. Even if a stepped portion is generated, the stepped portion can be made extremely small.

In addition, while pressing the heated original 10, the side of the surface 20B of the thermoplastic resin sheet 20 is heated for a certain period of time. Next, in the state in which the original 10 is pressed against the thermoplastic resin sheet 20, the original 10 is cooled until the thermoplastic resin sheet 20 is cooled to the softening temperature or lower.

Next, as illustrated in FIG. 16D, the original 10 and the thermoplastic resin sheet 20 are separated from each other, thereby forming the recessed pattern 20A having the inverted shape of the protruding pattern 10A on the surface 20B side of the thermoplastic resin sheet 20. The separation of the original 10 from the thermoplastic resin sheet 20 can be performed by the above-described Z-axis drive mechanism 32.

When the formation of the recessed pattern 20A in the region A1 in FIG. 16D is completed, alignment (here, a region A2) between the original 10 and the thermoplastic resin sheet 20 is performed. In the region A2, the heated original 10 is pressed against the surface 20B side of the thermoplastic resin sheet 20. The protruding pattern 10A of the original 10 is pressed against the surface 20B side of the thermoplastic resin sheet 20. When the original 10 is pressed against the surface 20B side of the thermoplastic resin sheet 20, the flat surface 10B of the original 10 and the surface 20B of the thermoplastic resin sheet 20 are separated from each other.

In the region A2, while pressing the heated original 10, the side of the surface 20B of the thermoplastic resin sheet 20 is heated for a certain period of time. Next, in the state in which the original 10 is pressed against the thermoplastic resin sheet 20, the original 10 is cooled until the thermoplastic resin sheet 20 is cooled to the softening temperature or lower. The original 10 and the thermoplastic resin sheet 20 are separated from each other, thereby forming the recessed pattern 20A having the inverted shape of the protruding pattern 10A on the surface 20B side of the thermoplastic resin sheet 20.

Furthermore, alignment (here, a region A3) between the original 10 and the thermoplastic resin sheet 20 is performed, and the heated original 10 is pressed against the surface 20B of the thermoplastic resin sheet 20.

The alignment process of the original 10 and the thermoplastic resin sheet 20 and the forming process of forming the recessed pattern 20A having the inverted shape of the protruding pattern 10A of the original 10 on the thermoplastic resin sheet 20, which are described with reference to FIGS. 16C and 16D, are repeated.

Figure 16E:
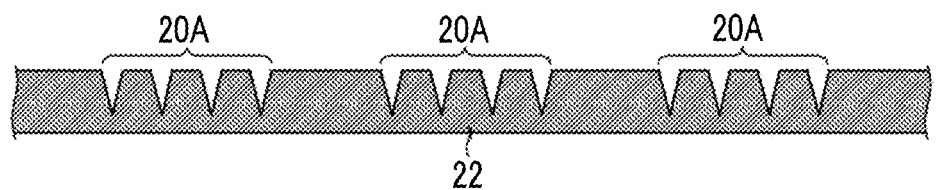
FIG. 16E is a sectional view of a mold produced in the production method of a large mold.

In addition, as illustrated in FIG. 16E, when the formation of the predetermined recessed pattern 20A on the surface 20B side of the thermoplastic resin sheet 20 is completed, the large mold 22 having a plurality of the recessed patterns 20A from the thermoplastic resin sheet 20 is produced.

Figure 17:
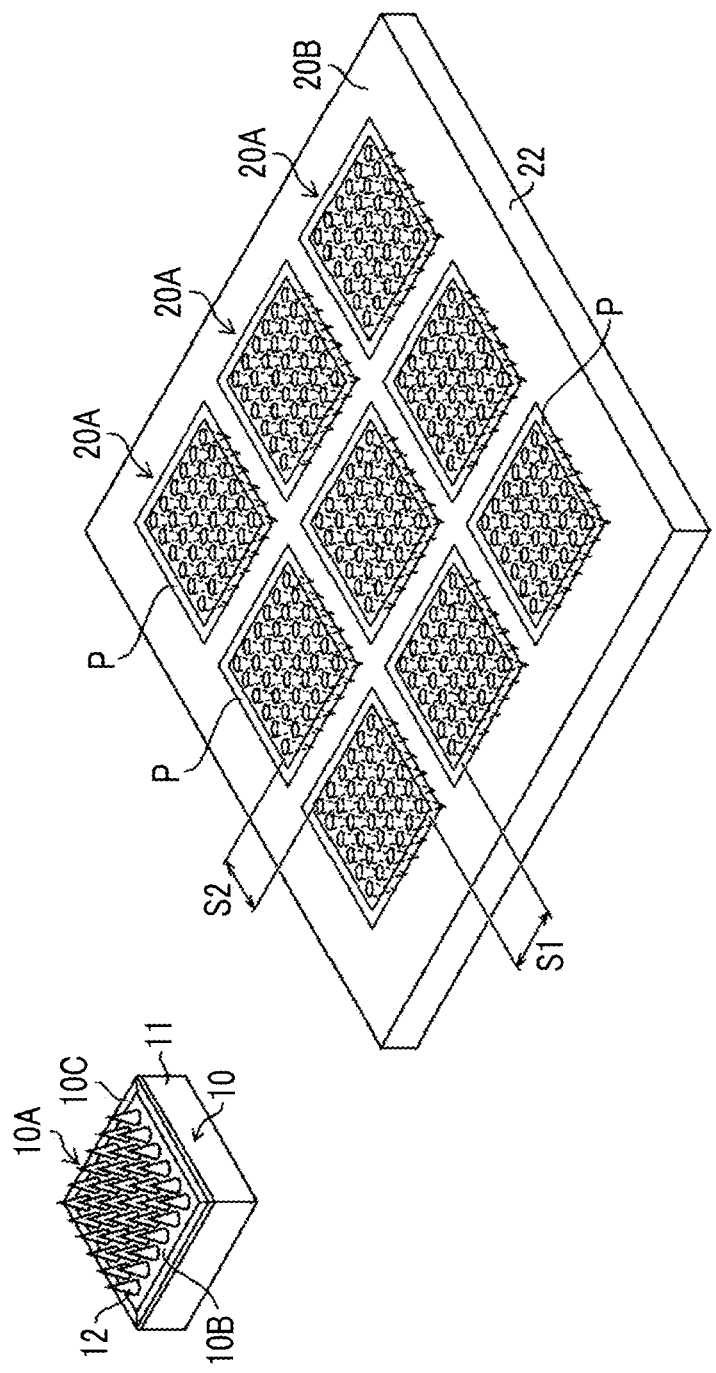
FIG. 17 is a perspective view of the original having one protruding pattern and the thermoplastic resin sheet having a plurality of recessed patterns.

FIG. 17 is a perspective view of the mold 22 produced according to FIGS. 16A to 16E and the original 10 having one protruding pattern 10A used for the mold 22.

As illustrated in FIG. 17, the mold 22 which has 3×3 recessed patterns 20A and is made of a resin is produced using the original 10 having one protruding pattern 10A. In this embodiment, when the mold 22 which has 3×3 recessed patterns 20A and is made of a resin is produced, a large original having 3×3 protruding patterns is not produced. Therefore, in this embodiment, the number of operations for producing the original 10 can be reduced. Although the mold 22 which has 3×3 recessed patterns 20A and is made of a resin is exemplified, the number of recessed patterns 20A is appropriately determined.

Furthermore, in this embodiment, since the mold 22 is produced using the original 10 having the inclined portion 10C, the generation of the stepped portion between adjacent recessed patterns 20A (for example, S1 and S2) can be prevented. Even if a stepped portion is generated, the stepped portion can be made extremely small. Accordingly, when a polymer sheet 210 is peeled away from the mold 22, the stepped portion does not become peeling resistance, and thus the polymer sheet 210 can be easily peeled away. Therefore, peeling failure such as breaking of the polymer sheet 210 does not occur.

[Manufacturing Method of Pattern Sheet] Next, a manufacturing method of a pattern sheet having a protruding pattern which is a formed product having a fine pattern using the large mold 22 produced as described above will be described. FIGS. 18A to 18G are process diagrams illustrating a procedure of the manufacturing method of a pattern sheet using the large mold 22.

Figure 18A:
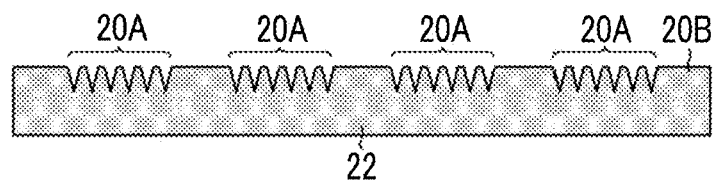
FIG. 18A is a diagram illustrating preparation of a mold in a process procedure of a manufacturing method of a pattern sheet.

FIG. 18A illustrates a state in which the mold 22 is prepared. The mold 22 is produced by the production method of a mold described above, and the plurality of recessed patterns 20A are formed on the surface 20B of the mold 22.

Figure 18B:
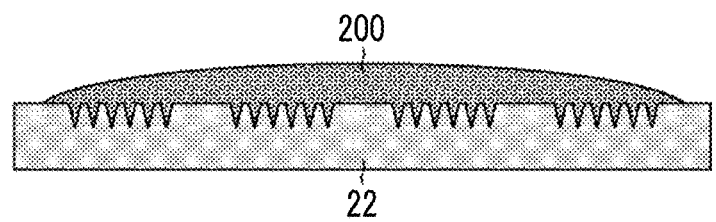
FIG. 18B is a diagram illustrating supply of a polymer solution to a recessed pattern in the process procedure of the manufacturing method of a pattern sheet.

FIG. 18B illustrates a supplying process of supplying a polymer solution to the plurality of recessed patterns 20A of the mold 22.

First, a polymer solution 200 is prepared. As a material of the resin polymer used for the polymer solution 200, it is preferable to use a biocompatible resin. As such resins, sugars such as glucose, maltose, pullulan, sodium chondroitin sulfate, sodium hyaluronate, hydroxyethyl starch, and hydroxypropyl cellulose, proteins such as gelatin and biodegradable polymers such as polylactic acid and a lactic acid-glycolic acid copolymer are preferably used. Among these, since gelatin-based materials have adhesion to many base materials and have a strong gel strength when used as a gelating material, the gelatin-based materials can be brought into close contact with a base material in the peeling process, which will be described later, and a polymer sheet can be peeled away from the mold 22 using the base material, so that the gelatin-based materials can be suitably used.

Furthermore, a drug may be contained in the polymer solution 200. The drug to be contained in the polymer solution 200 is not particularly limited as long as the drug is a substance having a physiological activity. The drug is preferably selected from peptides, proteins, nucleic acids, polysaccharides, vaccines, pharmaceutical compounds, or cosmetic ingredients. I addition, it is preferable that the pharmaceutical compound belongs to a water-soluble low molecular weight compound. Here, the low molecular weight compound is a compound having a molecular weight range of several hundreds to several thousands.

Although the concentration varies depending on the material, it is preferable that the concentration is set so that the resin polymer is contained at 10 to 50 mass % in the polymer solution 200 which does not contain the drug. The solvent used for dissolution may be warm water or may be volatile, and methyl ethyl ketone, alcohol, or the like may be used. And, it is possible to dissolve the drug, which is supplied into the body according to the application, in the solution of the polymer resin. The polymer concentration of the polymer solution 200 containing the drug (the concentration of the polymer excluding the drug when the drug itself is a polymer) is preferably in a range of 0 to 40 mass %.

As a method of preparing the polymer solution 200, in a case where a water-soluble polymer (such as gelatin) is used, a water-soluble powder may be dissolved in water and the drug may be added after the dissolution. Otherwise, a powder of a water-soluble polymer may be dissolved in a liquid in which the drug is dissolved. In a case where it is difficult to dissolve the polymer in water, heating may be performed for dissolution. The temperature can be appropriately selected depending on the kind of the polymer material, and it is preferable that heating is performed at a temperature of about 60° C. or lower. For the solution containing the drug, the viscosity of the solution of the polymer resin is preferably 100 Pa·s or less, and more preferably 10 Pa·s or less. For a solution which does not contain a drug, the viscosity is preferably 2000 Pa·s or less, and more preferably 1000 Pa·s or less. By appropriately adjusting the viscosity of the solution of the polymer resin, injecting the solution into a needle-like recess of a mold is facilitated. For example, the viscosity of the solution of the polymer resin can be measured with a capillary viscometer, a falling ball viscometer, a rotational viscometer, or a vibrational viscometer.

As illustrated in FIG. 18B, the polymer solution 200 is supplied to the mold 22 such that the plurality of recessed patterns 20A are filled with the polymer solution 200. That is, the recesses constituting the recessed patterns 20A are filled with the polymer solution 200.

As a method for filling the plurality of recessed patterns 20A with the polymer solution 200, a method of performing filling using a spin coater, a method of performing filling by moving a squeegee, a method of performing filling while moving a slit nozzle, a method of filling the recesses of the plurality of recessed patterns 20A using a dispenser, or the like may be employed.

As disclosed in WO2014/077242, it is preferable that in a state in which the slit nozzle is brought into contact with the surface of the mold 22, the polymer solution 200 is supplied to the plurality of recessed patterns 20A while moving the slit nozzle and the mold 22 relative to each other. In the case where the slit nozzle and the mold 22 are moved relative to each other in the state in which the slit nozzle is brought into contact with the surface of the mold 22, the surface of the mold 22 preferably has flatness.

A case where it is difficult for the polymer solution 200 to reach the corner of the recess of the recessed pattern 20A of the mold 22 due to the presence of the air is considered. Therefore, the supplying process is preferably performed under an environment at reduced pressure. The environment at reduced pressure means a state at or below atmospheric pressure. For example, by setting the mold 22 in a depressurization device (not illustrated) and supplying the polymer solution 200 to the mold 22, the polymer solution 200 can be supplied to the tip end of the recessed pattern 20A while the air is released from the recess under the environment at reduced pressure. This is particularly effective in a case where the mold 22 is a gas permeable material.

As another method, the mold 22 supplied with the polymer solution 200 is placed in a pressure vessel. After heating the inside of the pressure vessel to 40° C. using a heating jacket, compressed air is injected into the pressure vessel from a compressor. The air in the recess is removed by holding the inside of the pressure vessel at a pressure of 0.5 MPa for 5 minutes and applying a pressure thereto, thereby enabling the polymer solution 200 to be supplied to the tip end of the recessed pattern 20A of the mold 22.

Figure 18C:
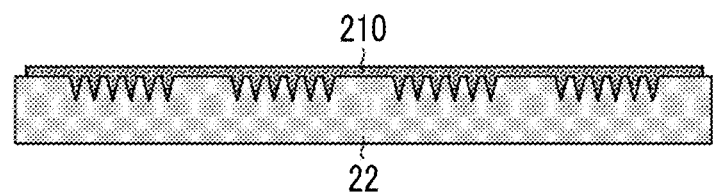
FIG. 18C is a diagram illustrating drying of the polymer solution in the process procedure of the manufacturing method of a pattern sheet.

FIG. 18C illustrates a drying process of drying the polymer solution 200 to form the polymer sheet 210. For example, the polymer solution 200 supplied to the mold 22 can be dried by blowing air thereto.

Drying is divided into, for example, four zones, and by setting conditions including (1) set dry at 15° C. (low humidity, wind speed 4 m/sec), (2) light wind drying at 35° C. (low humidity, wind speed 8 m/see), (3) strong wind drying at 50° C. (wind speed 12 m/sec), and (4) strong wind drying at 30° C. (wind speed 20 m/sec), efficient drying can be performed.

By gelating the polymer solution 200, the shape thereof can be reduced and a property of peeling the polymer solution 200 from the mold 22 can be enhanced. In this case, the polymer solution 200 can be gelated by flowing cold air at a low humidity. In order to completely gelate the polymer solution 200, cold air at 10 to 15 [° C.] is blown for a longer period of time than in the above case, and thereafter air is blown in the same manner as above. In addition, in this case, when hot air at a high temperature is flowed for subsequent drying, if the temperature of hot air is too high, gelation of the polymer solution 200 is cancelled or the effect of the drug may change due to decomposition of the drug through heating. Therefore, the temperature of the blown air requires attention. As described above, the applied polymer solution 200 is dried, or the polymer solution 200 is gelated and dried to solidify, thereby obtaining the polymer sheet 210.

By forming the polymer sheet 210, the polymer sheet 210 is reduced in size compared to the state when the polymer solution 200 is injected. Particularly, in a case where gelation is performed, the polymer sheet 210 is significantly reduced in size. Accordingly, peeling of the polymer sheet 210 from the mold 22 described later is facilitated.

The polymer sheet 210 means a state after a desired drying treatment is applied to the polymer solution 200. The moisture content of the polymer sheet 210 and the like are appropriately set.

Figure 18D:
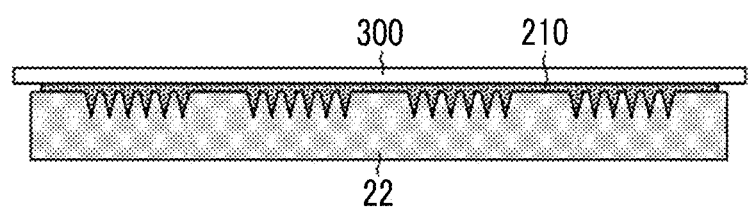
FIG. 18D is a diagram illustrating a polymer sheet before being peeled away from the mold in the process procedure of the manufacturing method of a pattern sheet.
Figure 18E:
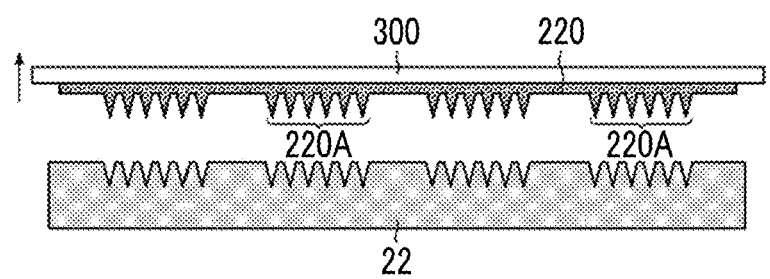
FIG. 18E is a diagram illustrating the polymer sheet after being peeled away from the mold in the process procedure of the manufacturing method of a pattern sheet.

FIGS. 18D and 18E illustrate a polymer sheet peeling process of peeling the polymer sheet 210 from the mold 22. As illustrated in FIG. 18D, a sheet-like base material 300 having a pressure sensitive adhesive layer formed thereon is attached to the surface of the polymer sheet 210 opposite to the mold 22. The surface of the base material 300 may be subjected to a surface activation treatment so as to be bonded. Furthermore, after the base material 300 is brought into close contact, the polymer solution may be applied thereto from above the base material 300 to bury the base material 300 therein. As a material of the sheet-like base material 300, for example, polyethylene terephthalate (PET), polypropylene (PP), polycarbonate (PC), or polyethylene (PE), may be used.

As illustrated in FIG. 18E, after the base material 300 is attached to the polymer sheet 210, the base material 300 and the polymer sheet 210 are simultaneously peeled away. A sucker (not illustrated) is placed on the surface of the base material 300 opposite to the bonding surface of the polymer sheet 210, and is pulled up vertically while sucking the base material 300 with air. The polymer sheet 210 is peeled away from the mold 22, thereby forming a pattern sheet 220 having a protruding pattern 220A.

In this peeling process, a stepped portion is not generated between adjacent recessed patterns 20A on the surface of the mold 22 or is extremely small even if the stepped portion is generated. Accordingly, the peeling property when the polymer sheet 210 is peeled away from the mold 22 is improved.

It is more preferable that the material forming the mold 22 is made of a material which can be very easily peeled away. Furthermore, by using a highly elastic and soft material as the material forming the mold 22, stress applied to the protruding pattern 220A of the pattern sheet 220 during peeling can be relieved.

The protruding pattern 220A of the pattern sheet 220 has the inverted shape of the recessed pattern 20A of the mold 22. Here, the pattern sheet 220 is basically the same as the polymer sheet 210 peeled away from the mold 22.

Figure 18F:
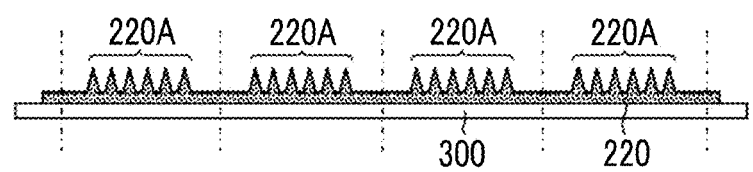
FIG. 18F is a diagram illustrating the polymer sheet before being cut into individual pattern sheets in the process procedure of the manufacturing method of a pattern sheet.
Figure 18G:
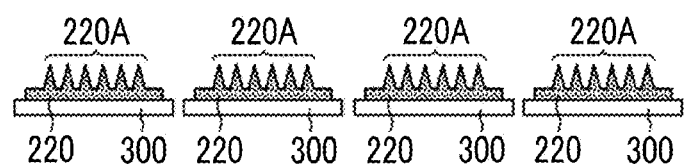
FIG. 18G is a diagram illustrating the polymer sheet after being cut into individual pattern sheets in the process procedure of the manufacturing method of a pattern sheet.

FIGS. 18F and 18G illustrate a cutting process of cutting the pattern sheet 220 into the individual pattern sheets 220.

As illustrated in FIG. 18F, the pattern sheet 220 having the protruding pattern 220A and the base material 300 peeled away from the mold 22 are set in a cutting device (not illustrated). The positions to cut the pattern sheet 220 are determined. Basically, the cutting position is determined for each protruding pattern 220A.

As illustrated in FIG. 18G, the pattern sheet 220 is cut into a plurality of the individual pattern sheets 220. In this embodiment, the example in which the pattern sheet 220 and the base material 300 are simultaneously cut is described, but the present invention is not limited thereto.

For example, the base material 300 may be peeled away from the pattern sheet 220 and the base material 300 peeled away from the mold 22, and the pattern sheet 220 may be cut into the individual pattern sheets 220.

In this embodiment, the case where the polymer sheet 210 is formed by filling the recessed pattern 20A with the polymer solution 200 and drying the polymer solution 200 is described, but the present invention is not limited thereto.

For example, a polymer sheet can be formed by filling the recessed pattern 20A with the polymer solution 200 containing the drug, drying the polymer solution 200, filling the recessed pattern 20A with the polymer solution 200 which does not contain a drug, and drying the polymer solution 200.

As long as the polymer solution 200 capable of forming the pattern sheet 220 is supplied, the number of times the polymer solution 200 is supplied and the presence or absence of the drug in the polymer solution 200 can be appropriately changed.

Figure 19:
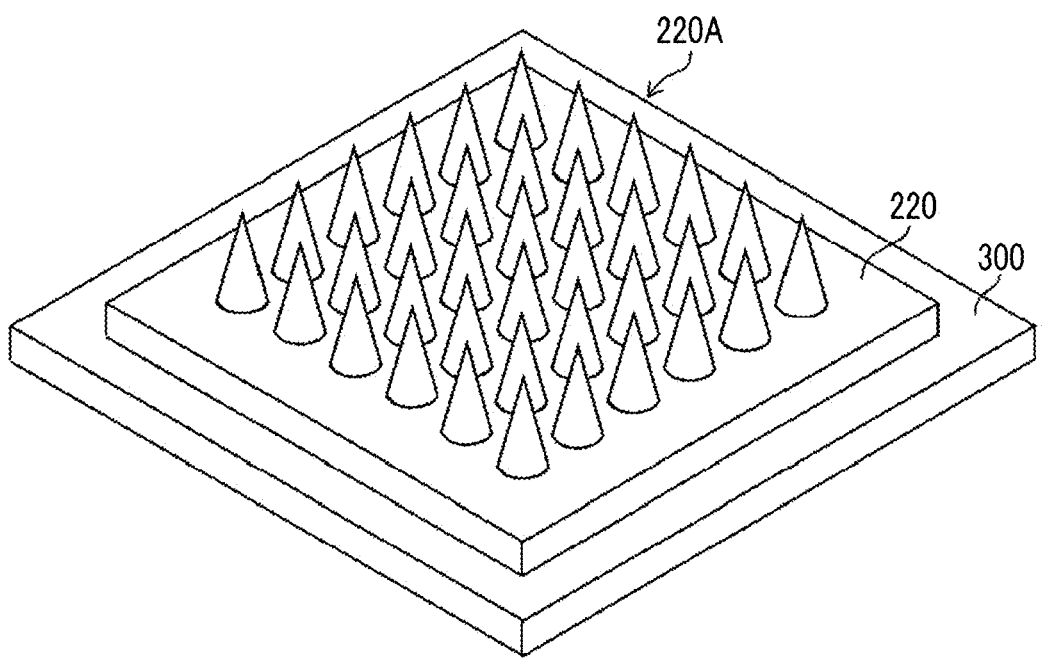
FIG. 19 is a perspective view of the individual pattern sheet.

FIG. 19 is a perspective view of the individual pattern sheet 220. The individual pattern sheet 220 has the protruding pattern 220A on one surface. In addition, the pattern sheet 220 has the base material 300 on the surface opposite to the surface on which the protruding pattern 220A is formed.

Figure 20A:
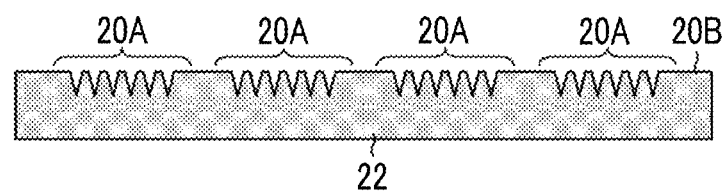
FIG. 20A is a diagram illustrating preparation of a mold in a process procedure of a production method of an electroform using a mold.
Figure 20B:
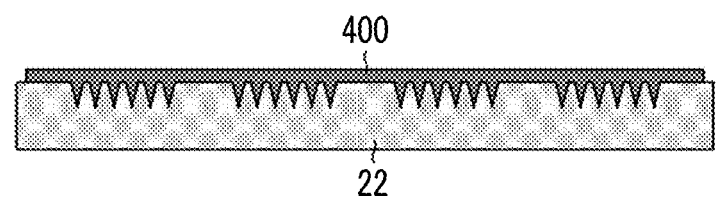
FIG. 20B is a diagram illustrating electroforming in the process procedure of the production method of an electroform using a mold.
Figure 20C:
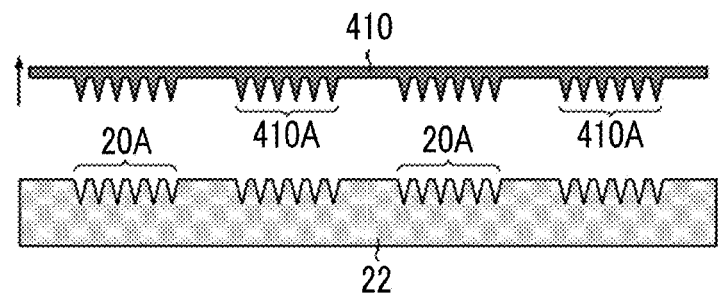
FIG. 20C is a diagram illustrating a metal body peeled away from the mold in the process procedure of the production method of an electroform using a mold.

[Production Method for Producing Electroform having Protruding Pattern] Next, a method of producing an electroform using the mold 22 will be described. FIGS. 20A to 20C are process diagrams illustrating a procedure of the production method of an electroform using the mold 22.

FIG. 20A illustrates a state in which the mold 22 is prepared. The mold 22 is produced by the above-described production method of the mold 22, and the recessed pattern 20A is formed on the surface 20B of the mold 22.

FIG. 20B is a process diagram illustrating an electroforming process in which metal is buried in the recessed pattern 20A of the mold 22 by an electroforming method. In the electroforming process, first, a conduction treatment is performed on the mold 22. Metal (for example, nickel) is sputtered onto the mold 22 to deposit the metal on the surface of the mold 22 and the recessed pattern 20A.

Next, the mold 22 subjected to the conduction treatment is held at a cathode. Metal pellets are held in a metallic case as an anode. The cathode holding the mold 22 and the anode holding the metal pellets are immersed in an electroforming liquid to cause electricity to flow. The metal is buried in the recessed pattern 20A of the mold 22 by the electroforming method, thereby forming a metal body 400. The electroforming method refers to a method of depositing metal on the surface of a mold by an electroplating method.

FIG. 20C is a process diagram illustrating a peeling process of peeling the metal body 400 from the mold 22. As illustrated in FIG. 20C, the metal body 400 is peeled away from the mold 22, thereby producing an electroform 410 having a protruding pattern 410A. Peeling means the separation of the metal body 400 from the mold 22. The protruding pattern 410A has the inverted shape of the recessed pattern 20A of the mold 22. Here, the electroform 410 is basically the same as the metal body 400 peeled away from the mold 22.

Even in the peeling process of peeling the metal body 400 from the mold 22, a stepped portion is not generated between adjacent recessed patterns 20A on the surface of the mold 22 or is extremely small even if the stepped portion is generated. Accordingly, the peeling property when the metal body 400 is peeled away from the mold 22 is improved.

In this embodiment, the mold 22 is produced using the original 10 illustrated in FIG. 1, and the electroform 410 is produced using the mold 22 illustrated in FIGS. 20A to 20C. Therefore, the electroform 410 having a larger area than the original 10 can be obtained. The electroform 410 has the same function as the original 10 and has a larger area than the original 10. That is, since an original having a large area can be obtained by an electroforming method other than machining such as grinding, the costs for producing the original having a large area can be reduced.

Figure 21A:
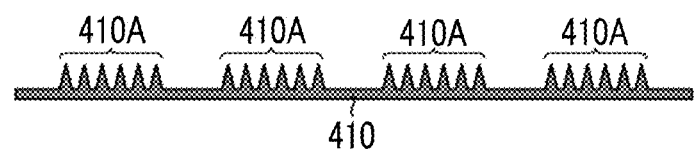
FIG. 21A is a diagram illustrating preparation of an electroform in a process procedure of a production method of a mold using an electroform.
Figure 21B:
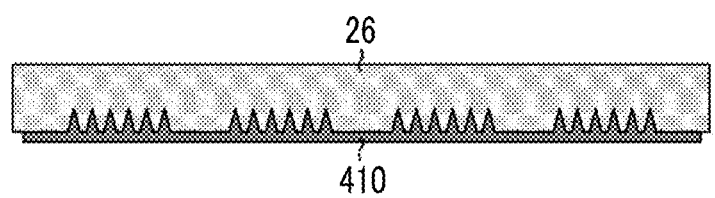
FIG. 21B is a diagram illustrating an ultraviolet curable resin which is pressed against the electroform in the process procedure of the production method of a mold using an electroform.
Figure 21C:
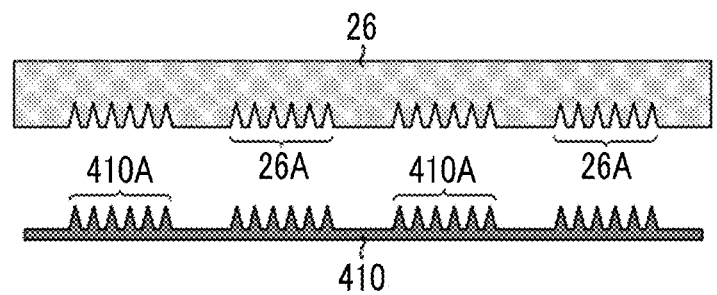
FIG. 21C is a diagram illustrating the electroform which is peeled away from the ultraviolet curable resin cured in the process procedure of the production method of a mold using an electroform.

Next, a method of producing a mold using the electroform 410 will be described. FIGS. 21A to 21C are process diagrams illustrating a procedure of the production method of the mold 26 using the electroform 410.

FIG. 21A illustrates a state in which the electroform 410 is prepared. The electroform 410 is produced by the above-described production method of the electroform 410. The electroform 410 has the protruding pattern 410A on one side.

FIGS. 21B and 21C are process diagrams illustrating a process of producing a mold 26 which has an recessed patterns 26A which has the inverted shape of the protruding pattern 410A of the electroform 410 and is made of a resin, by using the electroform 410 having the protruding pattern 410A. The recessed pattern 26A refers to a state in which recesses extending from one surface of the mold 26 toward the other surface are disposed on one surface of the mold 26. The number of recesses, the positions of the disposed recesses, and the like are not limited.

A method of producing the mold 26 using the electroform 410 will be described. The mold 26 having the recessed pattern 26A can be produced by the following first to third methods.

First, the first method will be described. An ultraviolet curable resin which is cured by being irradiated with ultraviolet rays is prepared. The protruding pattern 410A of the electroform 410 is pressed against the ultraviolet curable resin. In the state in which the electroform 410 is pressed against the ultraviolet curable resin, the ultraviolet curable resin is irradiated with ultraviolet rays such that the ultraviolet curable resin is cured. The electroform 410 is peeled away from the ultraviolet curable resin which is cured. The mold 26 having the recessed pattern 26A which has the inverted shape of the protruding pattern 410A of the electroform 410 and is made of the resin can be produced.

The second method will be described. A thermoplastic resin sheet as the material of the mold 26 is prepared. The electroform 410 having the protruding pattern 410A is heated. The protruding pattern 410A of the heated electroform 410 is pressed against the surface of the thermoplastic resin sheet. Since the surface of the thermoplastic resin is softened, the protruding pattern 410A is transferred onto the thermoplastic resin sheet.

In the state in which the electroform 410 is pressed against the thermoplastic resin sheet, the thermoplastic resin sheet and the electroform 410 are cooled. The thermoplastic resin sheet is cured by cooling the electroform 410. Thereafter, the electroform 410 is peeled away from the thermoplastic resin sheet to which the protruding pattern 410A has been transferred. The mold 26 having the recessed pattern 26A which has the inverted shape of the protruding pattern 410A of the electroform 410 and is made of the resin can be produced.

Next, the third method will be described. A silicone resin is prepared by adding a hardener to PDMS (polydimethylsiloxane, for example, SYLGARD 184 manufactured by Dow Corning Corporation). The protruding pattern 410A of the electroform 410 is pressed against the silicone resin. In the state in which the electroform 410 is pressed against the silicone resin, the silicone resin is heated and cured at 100° C. The electroform 410 is peeled away from the cured silicone resin. The mold 26 having the recessed pattern 26A which has the inverted shape of the protruding pattern 410A of the electroform 410 and is made of the resin can be produced.

Since the recessed pattern 26A has the inverted shape of the protruding pattern 410A, the size of each recess of the recessed pattern 26A is substantially the same as the size of the protrusion of the protruding pattern 410A. However, the method of producing the mold 26 is not limited to the first to third methods.

[Manufacturing Method of Pattern Sheet Using Mold Produced by Electroform] Next, a manufacturing method of a pattern sheet having a protruding pattern using the mold 26 produced as described above using the electroform 410 will be described. FIGS. 22A to 22G are process diagrams illustrating a procedure of the manufacturing method of the pattern sheet 220 using the mold 26. The process diagrams illustrating the procedure of the manufacturing method of the pattern sheet in FIGS. 18A to 18G and the process diagrams illustrating the procedure of the manufacturing method of the pattern sheet in FIGS. 22A to 22G are basically the same except for the difference between the mold 22 and the mold 26. Therefore, like configurations which are similar to those of the process diagrams illustrated in FIGS. 18A to 18G are denoted by like reference numerals, and the description thereof may be omitted in some cases.

Figure 22A:
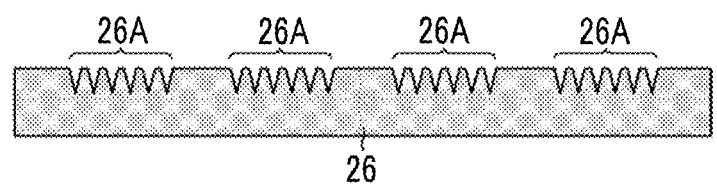
FIG. 22A is a diagram illustrating preparation of mold in a process procedure of a production method of a pattern sheet using a mold produced using an electroform.

FIG. 22A illustrates a state in which the mold 26 is prepared. As illustrated in FIGS. 21A to 21C described above, the mold 26 is produced using the electroform 410. The mold 26 has the recessed pattern 26A on one side.

Figure 22B:
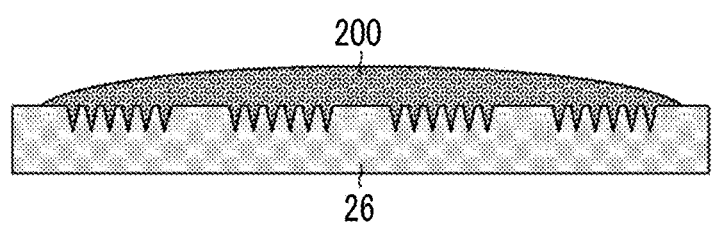
FIG. 22B is a diagram illustrating supply of a polymer solution to a recessed pattern in the process procedure of the production method of a pattern sheet using a mold produced using an electroform.

FIG. 22B illustrates a supplying process of supplying the polymer solution 200 to the recessed pattern 26A of the mold 26. The polymer solution 200 is basically the same as the polymer solution 200 described with reference to FIGS. 18A to 18G. As illustrated in FIG. 22B, the polymer solution 200 is supplied to the mold 26 such that the recessed pattern 26A is filled with the polymer solution 200. That is, the recesses constituting the recessed pattern 26A are filled with the polymer solution 200. As a method of filling the recesses of the recessed pattern 26A with the polymer solution 200, the filling methods described with reference to FIGS. 18A to 18G may be applied.

Figure 22C:
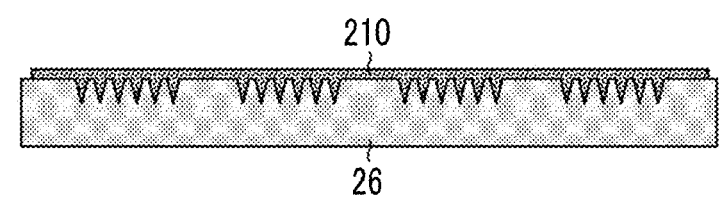
FIG. 22C is a diagram illustrating drying of the polymer solution in the process procedure of the production method of a pattern sheet using a mold produced using an electroform.

FIG. 22C illustrates a drying process of drying the polymer solution 200 to form the polymer sheet 210. For example, the polymer solution 200 supplied to the mold 26 can be dried by blowing air thereto. The drying method, conditions, and the like described with reference to FIGS. 18A to 18G can be applied.

Figure 22D:
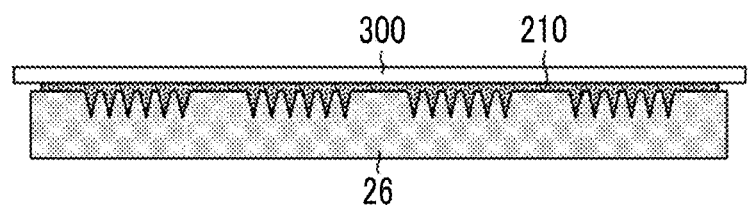
FIG. 22D is a diagram illustrating a polymer sheet before being peeled away from the mold in the process procedure of the production method of a pattern sheet using a mold produced using an electroform.
Figure 22E:
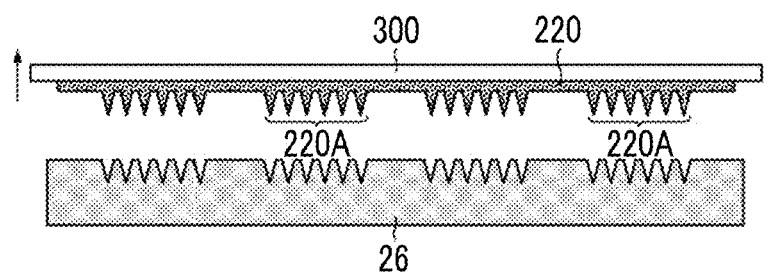
FIG. 22E is a diagram illustrating the polymer sheet after being peeled away from the mold in the process procedure of the production method of a pattern sheet using a mold produced using an electroform.

FIGS. 22D and 22E illustrate a polymer sheet peeling process of peeling the polymer sheet 210 from the mold 26. As illustrated in FIG. 22D, the sheet-like base material 300 having a pressure sensitive adhesive layer formed thereon is attached to the surface of the polymer sheet 210 opposite to the mold 26.

As illustrated in FIG. 22E, after the base material 300 is attached to the polymer sheet 210, the base material 300 and the polymer sheet 210 are simultaneously peeled away. A sucker (not illustrated) is placed on the surface of the base material 300 opposite to the bonding surface of the polymer sheet 210, and is pulled up vertically while sucking the base material 300 with air. The polymer sheet 210 is peeled away from the mold 26, thereby forming the pattern sheet 220 having the protruding pattern 220A.

It is more preferable that the material forming the mold 26 is made of a material which can be very easily peeled away. Furthermore, by using a highly elastic and soft material as the material forming the mold 26, stress applied to the protruding pattern 220A of the pattern sheet 220 during peeling can be relieved.

The protruding pattern 220A of the pattern sheet 220 has the inverted shape of the recessed pattern 26A of the mold 26. Here, the pattern sheet 220 is basically the same as the polymer sheet 210 peeled away from the mold 26.

Figure 22F:
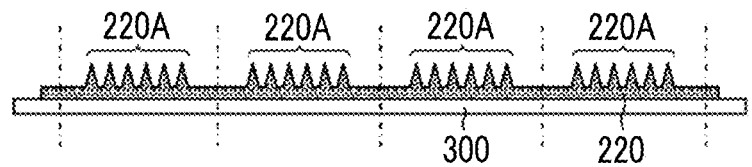
FIG. 22F is a diagram illustrating the polymer sheet before being cut into individual pattern sheets in the process procedure of the production method of a pattern sheet using a mold produced using an electroform.
Figure 22G:
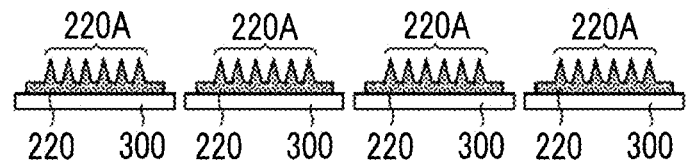
FIG. 22G is a diagram illustrating the polymer sheet after being cut into individual pattern sheets in the process procedure of the production method of a pattern sheet using a mold produced using an electroform.

FIGS. 22F and 22G illustrate a cutting process of cutting the pattern sheet 220 into the individual pattern sheets 220.

As illustrated in FIG. 22F, the pattern sheet 220 having the protruding pattern 220A and the base material 300 peeled away from the mold 26 are set in a cutting device (not illustrated). The positions to cut the pattern sheet 220 are determined. Basically, the cutting position is determined for each protruding pattern 220A.

As illustrated in FIG. 22G, the pattern sheet 220 is cut into a plurality of the individual pattern sheets 220. In this embodiment, the example in which the pattern sheet 220 and the base material 300 are simultaneously cut is described, but the present invention is not limited thereto.

For example, the base material 300 may be peeled away from the pattern sheet 220 and the base material 300 peeled away from the mold 26, and the pattern sheet 220 may be cut into the individual pattern sheets 220.

In this embodiment, the case where the polymer sheet 210 is formed by filling the recessed pattern 20A with the polymer solution 200 and drying the polymer solution 200 is described, but the present invention is not limited thereto.

For example, a polymer sheet can be formed by filling the recessed pattern 20A with the polymer solution 200 containing the drug, drying the polymer solution 200, filling the recessed pattern 20A with the polymer solution 200 which does not contain a drug, and drying the polymer solution 200.

As long as the polymer solution 200 capable of forming the pattern sheet 220 is supplied, the number of times the polymer solution 200 is supplied and the presence or absence of the drug in the polymer solution 200 can be appropriately changed.

As described above, according to this embodiment, the generation of a stepped portion between recessed patterns can be prevented, and even if a stepped portion is generated, the stepped portion can be made extremely small. In addition, the number of operations of producing the original can be reduced, and the productivity can be improved.

EXPLANATION OF REFERENCES

10: original
10A: protruding pattern
10B: flat surface
10C: inclined portion
10D: flat portion
11: base
12: protrusion
12A: needle portion
12B: frustum portion
12C: columnar portion
20: thermoplastic resin sheet
20A: recessed pattern
20B: surface
22: mold
23: duplicate mold (or formed product)
26: mold
26A: recessed pattern
30: pressing apparatus
32: Z-axis drive mechanism
34: connection portion
36: holding portion
38: table
40: X-axis drive mechanism
42: Y-axis drive mechanism
44: stand
46: control system
48: laser displacement meter
200: polymer solution
210: polymer sheet
220: pattern sheet
220A: protruding pattern
300: base material
400: metal body
410: electroform
410A: protruding pattern
P: raised portion

What is claimed is:

1. A production method of a mold comprising:
a preparation process of preparing an original having an inclined portion which is formed in an enclosed shape on an outer peripheral portion of a protruding pattern formed at a center portion on a base and gradually increases in thickness from inside toward outside, and a thermoplastic resin sheet; and
a forming process of forming a recessed pattern having an inverted shape of the protruding pattern on the thermoplastic resin sheet by pressing the original which is heated against the thermoplastic resin sheet at a position where the inclined portion of the original and a surface of the thermoplastic resin sheet are in close contact with each other, cooling the original in the state in which the original is pressed, and separating the original from the thermoplastic resin sheet, wherein a maximum thickness of the inclined portion is set so that a total volume of a portion of the protruding pattern which enters into the thermoplastic resin sheet when pressing the original against the thermoplastic resin sheet is equal to a total volume of spaces enclosed by the base, a surface of the thermoplastic resin sheet facing the original, and the inclined portion.

2. The production method of a mold according to claim 1, wherein an alignment process of determining a position at which the original is to be pressed against the thermoplastic resin sheet by moving the original and the thermoplastic resin sheet relative to each other, and the forming process are repeatedly performed.

3. The production method of a mold according to claim 1, wherein the inclined portion has a vertical sectional shape formed in a right-angled triangle such that the thickness thereof linearly increases from the inside toward the outside.

4. The production method of a mold according to claim 1, wherein the inclined portion has a vertical sectional shape formed in an arcuate shape such that the thickness thereof increases in an arc shape from the inside toward the outside and thereafter the increase in thickness gradually decreases.

5. The production method of a mold according to claim 1, wherein the original has a flat portion which is formed to be connected to an inclination terminal of the inclined portion.

6. The production method of a mold according to claim 1, wherein, when the original is pressed against the thermoplastic resin sheet, a position of the surface of the thermoplastic resin sheet is detected, and the original is pushed from the position of the surface of the thermoplastic resin sheet by a certain amount.

7. The production method of a mold according to claim 1, wherein, when the original is pressed against the thermoplastic resin sheet, a pressure applied to the original is measured and is compared to a certain pressure value which is set, and the amount of the original being pushed is determined.

8. A manufacturing method of a pattern sheet having a protruding pattern, comprising:
   a process of producing a mold using the production method according to claim 1;
   a supplying process of supplying a polymer solution to a recessed pattern of the mold;
   a drying process of drying the polymer solution to form a polymer sheet; and
   a polymer sheet peeling process of peeling the polymer sheet from the mold.

9. A production method of an electroform having a protruding pattern, comprising:
   a process of producing a mold using the production method according to claim 1;
   an electroforming process of forming a metal body on a recessed pattern of the mold by an electroforming method; and
   a peeling process of peeling the metal body from the mold.

10. A production method of a mold using an electroform, comprising:
    a process of producing an electroform using the production method according to claim 9; and
    a process of, by using the electroform having a protruding pattern, producing a mold which has a recessed pattern which is an inverted shape of the protruding pattern of the electroform and is made of a resin.

11. A manufacturing method of a pattern sheet having a protruding pattern, comprising:
    a process of producing a mold using the production method according to claim 10;
    a supplying process of supplying a polymer solution to a recessed pattern of the mold;
    a drying process of drying the polymer solution to form a polymer sheet; and
    a peeling process of peeling the polymer sheet from the mold.

* * * * *